(12) United States Patent
Krapcho et al.

(10) Patent No.: US 7,241,863 B2
(45) Date of Patent: Jul. 10, 2007

(54) HUMAN METABOTROPIC GLUTAMATE RECEPTOR

(75) Inventors: Karen J. Krapcho, Salt Lake City, UT (US); Thomas M. Stormann, Salt Lake City, UT (US); Cynthia Levinthal, Salt Lake City, UT (US); Lance G. Hammerland, Salt Lake City, UT (US); Laura Storjohann, Salt Lake City, UT (US)

(73) Assignee: NPS Pharmaceuticals, Inc., Salt Lake City, UT (US)

( * ) Notice: Subject to any disclaimer, the term of this patent is extended or adjusted under 35 U.S.C. 154(b) by 545 days.

(21) Appl. No.: 10/346,241

(22) Filed: Jan. 17, 2003

(65) Prior Publication Data

US 2003/0157647 A1  Aug. 21, 2003

(51) Int. Cl.
*C07K 14/00* (2006.01)
(52) U.S. Cl. .................. 530/350; 536/23.4; 435/69.1; 435/7.1
(58) Field of Classification Search ...... None
See application file for complete search history.

(56) References Cited

U.S. PATENT DOCUMENTS

| 5,385,831 A | 1/1995 | Mulvihill et al. |
| 5,521,297 A | 5/1996 | Daggett et al. |
| 5,750,369 A | 5/1998 | Lake et al. |
| 5,981,195 A | 11/1999 | Fuller et al. |
| 6,211,353 B1 * | 4/2001 | Burnett et al. ............. 536/23.5 |

FOREIGN PATENT DOCUMENTS

| WO | WO-94/29449 | 12/1994 |
| WO | WO-99/38975 | 8/1999 |

OTHER PUBLICATIONS

Aida et al. Molecular cloning of a putative Ca2+ sensing receptor cDNA from human kidney. Biochem. Biophys. Res. Commun., 1995, 214:524-529.*

Jonathan A. Javitch et al., "A Cysteine Residue in the Third Membrane-Spanning Segment of the Human $D_2$ Dopamine Receptor is Exposed in the Binding-Site Crevice," Proc. Nat'l. Acad. Sci. USA 91, vol. 91, pp. 10355-10359, Oct. 1994.

* cited by examiner

*Primary Examiner*—Gary B. Nickol
*Assistant Examiner*—Dong Jiang
(74) *Attorney, Agent, or Firm*—TraskBritt

(57) ABSTRACT

A novel human metabotropic glutamate receptor (mGluR) protein is identified, sequenced, and cloned. The receptor may be used to screen for compounds that modulate the activity of the mGluR. The recombinant mGluR, as well as compounds that modulate mGluR activity, may be used in the diagnosis and treatment of neurological disorders and diseases.

4 Claims, 5 Drawing Sheets

803
.....CFSVSLSATVALGCMFVPKVYIILAKP

TM VII

ERNVRSAFTTSTVVRMHVGDGKSSSAASRSSS

LVNLWKRRGSSGETLRYKDRRLAQHKSEIECF 895    896
TP/...../PSPFRDSVDSGSTTPNSPVSESA

Site of Deletion          942
LCIPSSPKYDTLIIRDYTQSSSSL

FIGURE 1A

KGSMGNGGRATMSSSNGKSVTWAQNEKSSRGQ
                    *              *

HLWQRLSIHINKKENPNQTAVIKPFPKSTESR

GLGPGRGAGGSAGGVGATGGAGCAGAGPGGPE

SPDAGPKALYDVAEAEEHFPAPARPRSPSPIS

TLSHRAGSASRTDDDVPSLHSEPVARSSSSQG

SLMEQISSVVTRFTANISELNSMMLSTAAPSP

GVGAPLCSSYLIPKEIQLPTTMTTFAEIQPLP

AIEVTGGAQPAAGAQAAGDAARESPAAGPEAA

AAKPDLEELVALTP

FIGURE 1B

SEQUENCE LISTING

<160> NUMBER OF SEQ ID NOS: 7

<210> SEQ ID NO 1
<211> LENGTH: 2826
<212> TYPE: DNA
<213> ORGANISM: Homo sapiens
<220> FEATURE:
<221> NAME/KEY: CDS
<222> LOCATION: (1)..(2826)

<400> SEQUENCE: 1

```
atg gtc ctt ctg ttg atc ctg tca gtc tta ctt ttg aaa gaa gat gtc      48
Met Val Leu Leu Leu Ile Leu Ser Val Leu Leu Leu Lys Glu Asp Val
 1               5                  10                  15 cgt ggg agt gca cag tcc agt gag agg agg gtg gtg gct cac atg ccg      96
Arg Gly Ser Ala Gln Ser Ser Glu Arg Arg Val Val Ala His Met Pro
            20                  25                  30 ggt gac atc att att gga gct ctc ttt tct gtt cat cac cag cct act     144
Gly Asp Ile Ile Ile Gly Ala Leu Phe Ser Val His His Gln Pro Thr
        35                  40                  45 gtg gac aaa gtt cat gag agg aag tgt ggg gcg gtc cgt gaa cag tat     192
Val Asp Lys Val His Glu Arg Lys Cys Gly Ala Val Arg Glu Gln Tyr
    50                  55                  60 ggc att cag aga gtg gag gcc atg ctg cat acc ctg gaa agg atc aat     240
Gly Ile Gln Arg Val Glu Ala Met Leu His Thr Leu Glu Arg Ile Asn
65                  70                  75                  80 tca gac ccc aca ctc ttg ccc aac atc aca ctg ggc tgt gag ata agg     288
Ser Asp Pro Thr Leu Leu Pro Asn Ile Thr Leu Gly Cys Glu Ile Arg
                85                  90                  95
```

-continued

| | |
|---|---|
| gac tcc tgc tgg cat tcg gct gtg gcc cta gag cag agc att gag ttc<br>Asp Ser Cys Trp His Ser Ala Val Ala Leu Glu Gln Ser Ile Glu Phe<br>100                            105                     110 | 336 |
| ata aga gat tcc ctc att tct tca gaa gag gaa gaa ggc ttg gta cgc<br>Ile Arg Asp Ser Leu Ile Ser Ser Glu Glu Glu Glu Gly Leu Val Arg<br>115                     120                     125 | 384 |
| tgt gtg gat ggc tcc tcc tct tcc ttc cgc tcc aag aag ccc ata gta<br>Cys Val Asp Gly Ser Ser Ser Ser Phe Arg Ser Lys Lys Pro Ile Val<br>130                     135                     140 | 432 |
| ggg gtc att ggg cct ggc tcc agt tct gta gcc att cag gtc cag aat<br>Gly Val Ile Gly Pro Gly Ser Ser Ser Val Ala Ile Gln Val Gln Asn<br>145                     150                     155                     160 | 480 |
| ttg ctc cag ctt ttc aac ata cct cag att gct tac tca gca acc agc<br>Leu Leu Gln Leu Phe Asn Ile Pro Gln Ile Ala Tyr Ser Ala Thr Ser<br>                  165                     170                     175 | 528 |
| atg gat ctg agt gac aag act ctg ttc aaa tat ttc atg agg gtt gtg<br>Met Asp Leu Ser Asp Lys Thr Leu Phe Lys Tyr Phe Met Arg Val Val<br>                  180                     185                     190 | 576 |
| cct tca gat gct cag cag gca agg gcc atg gtg gac ata gtg aag agg<br>Pro Ser Asp Ala Gln Gln Ala Arg Ala Met Val Asp Ile Val Lys Arg<br>195                     200                     205 | 624 |
| tac aac tgg acc tat gta tca gcc gtg cac aca gaa ggc aac tat gga<br>Tyr Asn Trp Thr Tyr Val Ser Ala Val His Thr Glu Gly Asn Tyr Gly<br>210                     215                     220 | 672 |
| gaa agt ggg atg gaa gcc ttc aaa gat atg tca gcg aag gaa ggg att<br>Glu Ser Gly Met Glu Ala Phe Lys Asp Met Ser Ala Lys Glu Gly Ile<br>225                     230                     235                     240 | 720 |
| tgc atc gcc cac tct tac aaa atc tac agt aat gca ggg gag cag agc<br>Cys Ile Ala His Ser Tyr Lys Ile Tyr Ser Asn Ala Gly Glu Gln Ser<br>                  245                     250                     255 | 768 |
| ttt gat aag ctg ctg aag aag ctc aca agt cac ttg ccc aag gcc cgg<br>Phe Asp Lys Leu Leu Lys Lys Leu Thr Ser His Leu Pro Lys Ala Arg<br>                  260                     265                     270 | 816 |
| gtg gtg gcc tgc ttc tgt gag ggc atg acg gtg aga ggt ctg ctg atg<br>Val Val Ala Cys Phe Cys Glu Gly Met Thr Val Arg Gly Leu Leu Met<br>275                     280                     285 | 864 |
| gcc atg agg cgc ctg ggt cta gcg gga gaa ttt ctg ctt ctg ggc agt<br>Ala Met Arg Arg Leu Gly Leu Ala Gly Glu Phe Leu Leu Leu Gly Ser<br>290                     295                     300 | 912 |
| gat ggc tgg gct gac agg tat gat gtg aca gat gga tat cag cga gaa<br>Asp Gly Trp Ala Asp Arg Tyr Asp Val Thr Asp Gly Tyr Gln Arg Glu<br>305                     310                     315                     320 | 960 |
| gct gtt ggt ggc atc aca atc aag ctc caa tct ccc gat gtc aag tgg<br>Ala Val Gly Gly Ile Thr Ile Lys Leu Gln Ser Pro Asp Val Lys Trp<br>                  325                     330                     335 | 1008 |
| ttt gat gat tat tat ctg aag ctc cgg cca gaa aca aac cac cga aac<br>Phe Asp Asp Tyr Tyr Leu Lys Leu Arg Pro Glu Thr Asn His Arg Asn<br>                  340                     345                     350 | 1056 |
| cct tgg ttt caa gaa ttt tgg cag cat cgt ttt cag tgc cga ctg gaa<br>Pro Trp Phe Gln Glu Phe Trp Gln His Arg Phe Gln Cys Arg Leu Glu<br>355                     360                     365 | 1104 |
| ggg ttt cca cag gag aac agc aaa tac aac aag act tgc aat agt tct<br>Gly Phe Pro Gln Glu Asn Ser Lys Tyr Asn Lys Thr Cys Asn Ser Ser<br>370                     375                     380 | 1152 |
| ctg act ctg aaa aca cat cat gtt cag gat tcc aaa atg gga ttt gtg<br>Leu Thr Leu Lys Thr His His Val Gln Asp Ser Lys Met Gly Phe Val<br>385                     390                     395                     400 | 1200 |
| atc aac gcc atc tat tcg atg gcc tat ggg ctc cac aac atg cag atg<br>Ile Asn Ala Ile Tyr Ser Met Ala Tyr Gly Leu His Asn Met Gln Met | 1248 |

-continued

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 405 |     |     |     |     | 410 |     |     |     |     | 415 |     |     |     |      |
| tcc | ctc | tgc | cca | ggc | tat | gca | gga | ctc | tgt | gat | gcc | atg | aag | cca | att | 1296 |
| Ser | Leu | Cys | Pro | Gly | Tyr | Ala | Gly | Leu | Cys | Asp | Ala | Met | Lys | Pro | Ile |      |
|     |     | 420 |     |     |     |     | 425 |     |     |     |     | 430 |     |     |     |      |
| gat | gga | cgg | aaa | ctt | ttg | gag | tcc | ctg | atg | aaa | acc | aat | ttt | act | ggg | 1344 |
| Asp | Gly | Arg | Lys | Leu | Leu | Glu | Ser | Leu | Met | Lys | Thr | Asn | Phe | Thr | Gly |      |
|     |     |     | 435 |     |     |     |     | 440 |     |     |     |     | 445 |     |     |      |
| gtt | tct | gga | gat | acg | atc | cta | ttc | gat | gag | aat | gga | gac | tct | cca | gga | 1392 |
| Val | Ser | Gly | Asp | Thr | Ile | Leu | Phe | Asp | Glu | Asn | Gly | Asp | Ser | Pro | Gly |      |
|     | 450 |     |     |     |     | 455 |     |     |     |     | 460 |     |     |     |     |      |
| agg | tat | gaa | ata | atg | aat | ttc | aag | gaa | atg | gga | aaa | gat | tac | ttt | gat | 1440 |
| Arg | Tyr | Glu | Ile | Met | Asn | Phe | Lys | Glu | Met | Gly | Lys | Asp | Tyr | Phe | Asp |      |
| 465 |     |     |     |     | 470 |     |     |     |     | 475 |     |     |     |     | 480 |      |
| tat | atc | aac | gtt | gga | agt | tgg | gac | aat | gga | gaa | tta | aaa | atg | gat | gat | 1488 |
| Tyr | Ile | Asn | Val | Gly | Ser | Trp | Asp | Asn | Gly | Glu | Leu | Lys | Met | Asp | Asp |      |
|     |     |     |     | 485 |     |     |     |     | 490 |     |     |     |     | 495 |     |      |
| gat | gaa | gta | tgg | tcc | aag | aaa | agc | aac | atc | atc | aga | tct | gtg | tgc | agt | 1536 |
| Asp | Glu | Val | Trp | Ser | Lys | Lys | Ser | Asn | Ile | Ile | Arg | Ser | Val | Cys | Ser |      |
|     |     |     | 500 |     |     |     |     | 505 |     |     |     |     | 510 |     |     |      |
| gaa | cca | tgt | gag | aaa | ggc | cag | atc | aag | gtg | atc | cga | aag | gga | gaa | gtc | 1584 |
| Glu | Pro | Cys | Glu | Lys | Gly | Gln | Ile | Lys | Val | Ile | Arg | Lys | Gly | Glu | Val |      |
|     |     | 515 |     |     |     |     | 520 |     |     |     |     | 525 |     |     |     |      |
| agc | tgt | tgt | tgg | acc | tgt | aca | cct | tgt | aag | gag | aat | gag | tat | gtc | ttt | 1632 |
| Ser | Cys | Cys | Trp | Thr | Cys | Thr | Pro | Cys | Lys | Glu | Asn | Glu | Tyr | Val | Phe |      |
|     | 530 |     |     |     |     | 535 |     |     |     |     | 540 |     |     |     |     |      |
| gat | gag | tac | aca | tgc | aag | gca | tgc | caa | ctg | ggg | tct | tgg | ccc | act | gat | 1680 |
| Asp | Glu | Tyr | Thr | Cys | Lys | Ala | Cys | Gln | Leu | Gly | Ser | Trp | Pro | Thr | Asp |      |
| 545 |     |     |     | 550 |     |     |     |     | 555 |     |     |     |     | 560 |     |      |
| gat | ctc | aca | ggt | tgt | gac | ttg | atc | cca | gta | cag | tat | ctt | cga | tgg | ggt | 1728 |
| Asp | Leu | Thr | Gly | Cys | Asp | Leu | Ile | Pro | Val | Gln | Tyr | Leu | Arg | Trp | Gly |      |
|     |     |     |     | 565 |     |     |     |     | 570 |     |     |     |     | 575 |     |      |
| gac | cct | gaa | ccc | att | gca | gct | gtg | gtg | ttt | gcc | tgc | ctt | ggc | ctc | ctg | 1776 |
| Asp | Pro | Glu | Pro | Ile | Ala | Ala | Val | Val | Phe | Ala | Cys | Leu | Gly | Leu | Leu |      |
|     |     |     | 580 |     |     |     |     | 585 |     |     |     |     | 590 |     |     |      |
| gcc | acc | ctg | ttt | gtt | act | gta | gtc | ttc | atc | att | tac | cgt | gat | aca | cca | 1824 |
| Ala | Thr | Leu | Phe | Val | Thr | Val | Val | Phe | Ile | Ile | Tyr | Arg | Asp | Thr | Pro |      |
|     | 595 |     |     |     |     | 600 |     |     |     |     | 605 |     |     |     |     |      |
| gta | gtc | aag | tcc | tca | agc | agg | gaa | ctc | tgc | tac | att | atc | ctt | gct | ggc | 1872 |
| Val | Val | Lys | Ser | Ser | Ser | Arg | Glu | Leu | Cys | Tyr | Ile | Ile | Leu | Ala | Gly |      |
| 610 |     |     |     |     | 615 |     |     |     |     | 620 |     |     |     |     |     |      |
| atc | tgc | ctg | ggc | tac | tta | tgt | acc | ttc | tgc | ctc | att | gcg | aag | ccc | aaa | 1920 |
| Ile | Cys | Leu | Gly | Tyr | Leu | Cys | Thr | Phe | Cys | Leu | Ile | Ala | Lys | Pro | Lys |      |
| 625 |     |     |     | 630 |     |     |     |     | 635 |     |     |     |     | 640 |     |      |
| cag | att | tac | tgc | tac | ctt | cag | aga | att | ggc | att | ggt | ctc | tcc | cca | gcc | 1968 |
| Gln | Ile | Tyr | Cys | Tyr | Leu | Gln | Arg | Ile | Gly | Ile | Gly | Leu | Ser | Pro | Ala |      |
|     |     |     |     | 645 |     |     |     |     | 650 |     |     |     |     | 655 |     |      |
| atg | agc | tac | tca | gcc | ctt | gta | aca | aag | acc | aac | cgt | att | gca | agg | atc | 2016 |
| Met | Ser | Tyr | Ser | Ala | Leu | Val | Thr | Lys | Thr | Asn | Arg | Ile | Ala | Arg | Ile |      |
|     |     |     | 660 |     |     |     |     | 665 |     |     |     |     | 670 |     |     |      |
| ctg | gct | ggc | agc | aag | aag | aag | atc | tgt | acc | aaa | aag | ccc | aga | ttc | atg | 2064 |
| Leu | Ala | Gly | Ser | Lys | Lys | Lys | Ile | Cys | Thr | Lys | Lys | Pro | Arg | Phe | Met |      |
|     |     | 675 |     |     |     |     | 680 |     |     |     |     | 685 |     |     |     |      |
| agt | gcc | tgt | gcc | cag | cta | gtg | att | gct | ttc | att | ctc | ata | tgc | atc | cag | 2112 |
| Ser | Ala | Cys | Ala | Gln | Leu | Val | Ile | Ala | Phe | Ile | Leu | Ile | Cys | Ile | Gln |      |
|     | 690 |     |     |     |     | 695 |     |     |     |     | 700 |     |     |     |     |      |
| ttg | ggc | atc | atc | gtt | gcc | ctc | ttt | ata | atg | gag | cct | cct | gac | ata | atg | 2160 |
| Leu | Gly | Ile | Ile | Val | Ala | Leu | Phe | Ile | Met | Glu | Pro | Pro | Asp | Ile | Met |      |
| 705 |     |     |     | 710 |     |     |     |     | 715 |     |     |     |     | 720 |     |      |
| cat | gac | tac | cca | agc | att | cga | gaa | gtc | tac | ctg | atc | tgt | aac | acc | acc | 2208 |

-continued

```
His Asp Tyr Pro Ser Ile Arg Glu Val Tyr Leu Ile Cys Asn Thr Thr
            725                 730                 735 aac cta gga gtt gtc act cca ctt gga tac aat gga ttg ttg att ttg        2256
Asn Leu Gly Val Val Thr Pro Leu Gly Tyr Asn Gly Leu Leu Ile Leu
        740                 745                 750 agc tgc acc ttc tat gcg ttc aag acc aga aat gtt cca gct aac ttc        2304
Ser Cys Thr Phe Tyr Ala Phe Lys Thr Arg Asn Val Pro Ala Asn Phe
            755                 760                 765 aac gag gcc aag tat atc gcc ttc aca atg tac acg acc tgc att ata        2352
Asn Glu Ala Lys Tyr Ile Ala Phe Thr Met Tyr Thr Thr Cys Ile Ile
    770                 775                 780 tgg cta gct ttt gtg cca atc tac ttt ggc agc aac tac aaa atc atc        2400
Trp Leu Ala Phe Val Pro Ile Tyr Phe Gly Ser Asn Tyr Lys Ile Ile
785                 790                 795                 800 acc atg tgt ttc tcg gtc agc ctc agt gcc aca gtg gcc cta ggc tgc        2448
Thr Met Cys Phe Ser Val Ser Leu Ser Ala Thr Val Ala Leu Gly Cys
                805                 810                 815 atg ttt gtg ccg aag gtg tac atc atc ctg gcc aaa cca gag aga aac        2496
Met Phe Val Pro Lys Val Tyr Ile Ile Leu Ala Lys Pro Glu Arg Asn
            820                 825                 830 gtg cgc agc gcc ttc acc aca tct acc gtg gtg cgc atg cat gta ggg        2544
Val Arg Ser Ala Phe Thr Thr Ser Thr Val Val Arg Met His Val Gly
        835                 840                 845 gat ggc aag tca tcc tcc gca gcc agc aga tcc agc agc cta gtc aac        2592
Asp Gly Lys Ser Ser Ser Ala Ala Ser Arg Ser Ser Ser Leu Val Asn
    850                 855                 860 ctg tgg aag aga agg ggc tcc tct ggg gaa acc tta agg tac aaa gac        2640
Leu Trp Lys Arg Arg Gly Ser Ser Gly Glu Thr Leu Arg Tyr Lys Asp
865                 870                 875                 880 agg aga ctg gcc cag cac aag tcg gaa ata gag tgt ttc acc ccg ccg        2688
Arg Arg Leu Ala Gln His Lys Ser Glu Ile Glu Cys Phe Thr Pro Pro
                885                 890                 895 tcc ccc ttc aga gac tcg gtg gac tcg ggg agc aca acc ccc aac tcg        2736
Ser Pro Phe Arg Asp Ser Val Asp Ser Gly Ser Thr Thr Pro Asn Ser
            900                 905                 910 cca gtg tcc gag tcg gcc ctc tgt atc ccg tcg tct ccc aaa tat gac        2784
Pro Val Ser Glu Ser Ala Leu Cys Ile Pro Ser Ser Pro Lys Tyr Asp
        915                 920                 925 act ctt atc ata aga gat tac act cag agc tcc tcg tcg ttg                2826
Thr Leu Ile Ile Arg Asp Tyr Thr Gln Ser Ser Ser Ser Leu
    930                 935                 940

<210> SEQ ID NO 2
<211> LENGTH: 942
<212> TYPE: PRT
<213> ORGANISM: Homo sapiens

<400> SEQUENCE: 2

Met Val Leu Leu Leu Ile Leu Ser Val Leu Leu Lys Glu Asp Val
1               5                   10                  15

Arg Gly Ser Ala Gln Ser Ser Glu Arg Arg Val Val Ala His Met Pro
            20                  25                  30

Gly Asp Ile Ile Ile Gly Ala Leu Phe Ser Val His His Gln Pro Thr
        35                  40                  45

Val Asp Lys Val His Glu Arg Lys Cys Gly Ala Val Arg Glu Gln Tyr
    50                  55                  60

Gly Ile Gln Arg Val Glu Ala Met Leu His Thr Leu Glu Arg Ile Asn
65                  70                  75                  80

Ser Asp Pro Thr Leu Leu Pro Asn Ile Thr Leu Gly Cys Glu Ile Arg
```

-continued

```
                    85                  90                  95
Asp Ser Cys Trp His Ser Ala Val Ala Leu Glu Gln Ser Ile Glu Phe
                100                 105                 110
Ile Arg Asp Ser Leu Ile Ser Ser Glu Glu Glu Gly Leu Val Arg
                115                 120                 125
Cys Val Asp Gly Ser Ser Ser Phe Arg Ser Lys Lys Pro Ile Val
130                 135                 140
Gly Val Ile Gly Pro Gly Ser Ser Val Ala Ile Gln Val Gln Asn
145                 150                 155                 160
Leu Leu Gln Leu Phe Asn Ile Pro Gln Ile Ala Tyr Ser Ala Thr Ser
                165                 170                 175
Met Asp Leu Ser Asp Lys Thr Leu Phe Lys Tyr Phe Met Arg Val Val
                180                 185                 190
Pro Ser Asp Ala Gln Gln Ala Arg Ala Met Val Asp Ile Val Lys Arg
                195                 200                 205
Tyr Asn Trp Thr Tyr Val Ser Ala Val His Thr Glu Gly Asn Tyr Gly
                210                 215                 220
Glu Ser Gly Met Glu Ala Phe Lys Asp Met Ser Ala Lys Glu Gly Ile
225                 230                 235                 240
Cys Ile Ala His Ser Tyr Lys Ile Tyr Ser Asn Ala Gly Glu Gln Ser
                245                 250                 255
Phe Asp Lys Leu Leu Lys Lys Leu Thr Ser His Leu Pro Lys Ala Arg
                260                 265                 270
Val Val Ala Cys Phe Cys Glu Gly Met Thr Val Arg Gly Leu Leu Met
                275                 280                 285
Ala Met Arg Arg Leu Gly Leu Ala Gly Glu Phe Leu Leu Leu Gly Ser
290                 295                 300
Asp Gly Trp Ala Asp Arg Tyr Asp Val Thr Asp Gly Tyr Gln Arg Glu
305                 310                 315                 320
Ala Val Gly Gly Ile Thr Ile Lys Leu Gln Ser Pro Asp Val Lys Trp
                325                 330                 335
Phe Asp Asp Tyr Tyr Leu Lys Leu Arg Pro Glu Thr Asn His Arg Asn
                340                 345                 350
Pro Trp Phe Gln Glu Phe Trp Gln His Arg Phe Gln Cys Arg Leu Glu
                355                 360                 365
Gly Phe Pro Gln Glu Asn Ser Lys Tyr Asn Lys Thr Cys Asn Ser Ser
                370                 375                 380
Leu Thr Leu Lys Thr His His Val Gln Asp Ser Lys Met Gly Phe Val
385                 390                 395                 400
Ile Asn Ala Ile Tyr Ser Met Ala Tyr Gly Leu His Asn Met Gln Met
                405                 410                 415
Ser Leu Cys Pro Gly Tyr Ala Gly Leu Cys Asp Ala Met Lys Pro Ile
                420                 425                 430
Asp Gly Arg Lys Leu Leu Glu Ser Leu Met Lys Thr Asn Phe Thr Gly
                435                 440                 445
Val Ser Gly Asp Thr Ile Leu Phe Asp Glu Asn Gly Asp Ser Pro Gly
450                 455                 460
Arg Tyr Glu Ile Met Asn Phe Lys Glu Met Gly Lys Asp Tyr Phe Asp
465                 470                 475                 480
Tyr Ile Asn Val Gly Ser Trp Asp Asn Gly Glu Leu Lys Met Asp Asp
                485                 490                 495
Asp Glu Val Trp Ser Lys Lys Ser Asn Ile Ile Arg Ser Val Cys Ser
                500                 505                 510
```

```
Glu Pro Cys Glu Lys Gly Gln Ile Lys Val Ile Arg Lys Gly Glu Val
            515                 520                 525

Ser Cys Cys Trp Thr Cys Thr Pro Cys Lys Glu Asn Glu Tyr Val Phe
        530                 535                 540

Asp Glu Tyr Thr Cys Lys Ala Cys Gln Leu Gly Ser Trp Pro Thr Asp
545                 550                 555                 560

Asp Leu Thr Gly Cys Asp Leu Ile Pro Val Gln Tyr Leu Arg Trp Gly
                565                 570                 575

Asp Pro Glu Pro Ile Ala Ala Val Val Phe Ala Cys Leu Gly Leu Leu
            580                 585                 590

Ala Thr Leu Phe Val Thr Val Val Phe Ile Ile Tyr Arg Asp Thr Pro
        595                 600                 605

Val Val Lys Ser Ser Arg Glu Leu Cys Tyr Ile Ile Leu Ala Gly
            610                 615                 620

Ile Cys Leu Gly Tyr Leu Cys Thr Phe Cys Leu Ile Ala Lys Pro Lys
625                 630                 635                 640

Gln Ile Tyr Cys Tyr Leu Gln Arg Ile Gly Ile Gly Leu Ser Pro Ala
                645                 650                 655

Met Ser Tyr Ser Ala Leu Val Thr Lys Thr Asn Arg Ile Ala Arg Ile
            660                 665                 670

Leu Ala Gly Ser Lys Lys Ile Cys Thr Lys Pro Arg Phe Met
        675                 680                 685

Ser Ala Cys Ala Gln Leu Val Ile Ala Phe Ile Leu Ile Cys Ile Gln
        690                 695                 700

Leu Gly Ile Ile Val Ala Leu Phe Ile Met Glu Pro Pro Asp Ile Met
705                 710                 715                 720

His Asp Tyr Pro Ser Ile Arg Glu Val Tyr Leu Ile Cys Asn Thr Thr
                725                 730                 735

Asn Leu Gly Val Val Thr Pro Leu Gly Tyr Asn Gly Leu Leu Ile Leu
            740                 745                 750

Ser Cys Thr Phe Tyr Ala Phe Lys Thr Arg Asn Val Pro Ala Asn Phe
        755                 760                 765

Asn Glu Ala Lys Tyr Ile Ala Phe Thr Met Tyr Thr Thr Cys Ile Ile
770                 775                 780

Trp Leu Ala Phe Val Pro Ile Tyr Phe Gly Ser Asn Tyr Lys Ile Ile
785                 790                 795                 800

Thr Met Cys Phe Ser Val Ser Leu Ser Ala Thr Val Ala Leu Gly Cys
            805                 810                 815

Met Phe Val Pro Lys Val Tyr Ile Ile Leu Ala Lys Pro Glu Arg Asn
            820                 825                 830

Val Arg Ser Ala Phe Thr Thr Ser Thr Val Val Arg Met His Val Gly
        835                 840                 845

Asp Gly Lys Ser Ser Ser Ala Ala Ser Arg Ser Ser Ser Leu Val Asn
            850                 855                 860

Leu Trp Lys Arg Arg Gly Ser Ser Gly Glu Thr Leu Arg Tyr Lys Asp
865                 870                 875                 880

Arg Arg Leu Ala Gln His Lys Ser Glu Ile Glu Cys Phe Thr Pro Pro
                885                 890                 895

Ser Pro Phe Arg Asp Ser Val Asp Ser Gly Ser Thr Thr Pro Asn Ser
            900                 905                 910

Pro Val Ser Glu Ser Ala Leu Cys Ile Pro Ser Ser Pro Lys Tyr Asp
            915                 920                 925
```

```
                Thr Leu Ile Ile Arg Asp Tyr Thr Gln Ser Ser Ser Ser Leu
                    930                 935                 940

<210> SEQ ID NO 3
<211> LENGTH: 2925
<212> TYPE: DNA
<213> ORGANISM: Artificial Sequence
<220> FEATURE:
<221> NAME/KEY: CDS
<222> LOCATION: (1)..(2925)
<223> OTHER INFORMATION: Description of Artificial Sequence:Chimeric
      molecule comprising portions of the human calcium
      receptor and human mGluR5d.

<400> SEQUENCE: 3 atg gca ttt tat agc tgc tgc tgg gtc ctc ttg gca ctc acc tgg cac        48
Met Ala Phe Tyr Ser Cys Cys Trp Val Leu Leu Ala Leu Thr Trp His
  1               5                  10                  15 acc tct gcc tac ggg cca gac cag cga gcc caa aag aag ggg gac att        96
Thr Ser Ala Tyr Gly Pro Asp Gln Arg Ala Gln Lys Lys Gly Asp Ile
             20                  25                  30 atc ctt ggg ggg ctc ttt cct att cat ttt gga gta gca gct aaa gat       144
Ile Leu Gly Gly Leu Phe Pro Ile His Phe Gly Val Ala Ala Lys Asp
         35                  40                  45 caa gat ctc aaa tca agg ccg gag tct gtg gaa tgt atc agg tat aat       192
Gln Asp Leu Lys Ser Arg Pro Glu Ser Val Glu Cys Ile Arg Tyr Asn
     50                  55                  60 ttc cgt ggg ttt cgc tgg tta cag gct atg ata ttt gcc ata gag gag       240
Phe Arg Gly Phe Arg Trp Leu Gln Ala Met Ile Phe Ala Ile Glu Glu
 65                  70                  75                  80 ata aac agc agc cca gcc ctt ctt ccc aac ttg acg ctg gga tac agg       288
Ile Asn Ser Ser Pro Ala Leu Leu Pro Asn Leu Thr Leu Gly Tyr Arg
                 85                  90                  95 ata ttt gac act tgc aac acc gtt tct aag gcc ttg gaa gcc acc ctg       336
Ile Phe Asp Thr Cys Asn Thr Val Ser Lys Ala Leu Glu Ala Thr Leu
            100                 105                 110 agt ttt gtt gct caa aac aaa att gat tct ttg aac ctt gat gag ttc       384
Ser Phe Val Ala Gln Asn Lys Ile Asp Ser Leu Asn Leu Asp Glu Phe
        115                 120                 125 tgc aac tgc tca gag cac att ccc tct acg att gct gtg gtg gga gca       432
Cys Asn Cys Ser Glu His Ile Pro Ser Thr Ile Ala Val Val Gly Ala
    130                 135                 140 act ggc tca ggc gtc tcc acg gca gtg gca aat ctg ctg ggg ctc ttc       480
Thr Gly Ser Gly Val Ser Thr Ala Val Ala Asn Leu Leu Gly Leu Phe
145                 150                 155                 160 tac att ccc cag gtc agt tat gcc tcc tcc agc aga ctc ctc agc aac       528
Tyr Ile Pro Gln Val Ser Tyr Ala Ser Ser Ser Arg Leu Leu Ser Asn
                165                 170                 175 aag aat caa ttc aag tct ttc ctc cga acc atc ccc aat gat gag cac       576
Lys Asn Gln Phe Lys Ser Phe Leu Arg Thr Ile Pro Asn Asp Glu His
            180                 185                 190 cag gcc act gcc atg gca gac atc atc gag tat ttc cgc tgg aac tgg       624
Gln Ala Thr Ala Met Ala Asp Ile Ile Glu Tyr Phe Arg Trp Asn Trp
        195                 200                 205 gtg ggc aca att gca gct gat gac gac tat ggg cgg ccg ggg att gag       672
Val Gly Thr Ile Ala Ala Asp Asp Asp Tyr Gly Arg Pro Gly Ile Glu
    210                 215                 220 aaa ttc cga gag gaa gct gag gaa agg gat atc tgc atc gac ttc agt       720
Lys Phe Arg Glu Glu Ala Glu Glu Arg Asp Ile Cys Ile Asp Phe Ser
225                 230                 235                 240 gaa ctc atc tcc cag tac tct gat gag gaa gag atc cag cat gtg gta       768
Glu Leu Ile Ser Gln Tyr Ser Asp Glu Glu Glu Ile Gln His Val Val
```

```
                    245                 250                 255
gag gtg att caa aat tcc acg gcc aaa gtc atc gtg gtt ttc tcc agt              816
Glu Val Ile Gln Asn Ser Thr Ala Lys Val Ile Val Val Phe Ser Ser
            260                 265                 270 ggc cca gat ctt gag ccc ctc atc aag gag att gtc cgg cgc aat atc              864
Gly Pro Asp Leu Glu Pro Leu Ile Lys Glu Ile Val Arg Arg Asn Ile
        275                 280                 285 acg ggc aag atc tgg ctg gcc agc gag gcc tgg gcc agc tcc tcc ctg              912
Thr Gly Lys Ile Trp Leu Ala Ser Glu Ala Trp Ala Ser Ser Ser Leu
    290                 295                 300 atc gcc atg cct cag tac ttc cac gtg gtt ggc ggc acc att gga ttc              960
Ile Ala Met Pro Gln Tyr Phe His Val Val Gly Gly Thr Ile Gly Phe
305                 310                 315                 320 gct ctg aag gct ggg cag atc cca ggc ttc cgg gaa ttc ctg aag aag             1008
Ala Leu Lys Ala Gly Gln Ile Pro Gly Phe Arg Glu Phe Leu Lys Lys
                325                 330                 335 gtc cat ccc agg aag tct gtc cac aat ggt ttt gcc aag gag ttt tgg             1056
Val His Pro Arg Lys Ser Val His Asn Gly Phe Ala Lys Glu Phe Trp
            340                 345                 350 gaa gaa aca ttt aac tgc cac ctc caa gaa ggt gca aaa gga cct tta             1104
Glu Glu Thr Phe Asn Cys His Leu Gln Glu Gly Ala Lys Gly Pro Leu
        355                 360                 365 cct gtg gac acc ttt ctg aga ggt cac gaa gaa agt ggc gac agg ttt             1152
Pro Val Asp Thr Phe Leu Arg Gly His Glu Glu Ser Gly Asp Arg Phe
    370                 375                 380 agc aac agc tcg aca gcc ttc cga ccc ctc tgt aca ggg gat gag aac             1200
Ser Asn Ser Ser Thr Ala Phe Arg Pro Leu Cys Thr Gly Asp Glu Asn
385                 390                 395                 400 atc agc agt gtc gag acc cct tac ata gat tac acg cat tta cgg ata             1248
Ile Ser Ser Val Glu Thr Pro Tyr Ile Asp Tyr Thr His Leu Arg Ile
                405                 410                 415 tcc tac aat gtg tac tta gca gtc tac tcc att gcc cac gcc ttg caa             1296
Ser Tyr Asn Val Tyr Leu Ala Val Tyr Ser Ile Ala His Ala Leu Gln
            420                 425                 430 gat ata tat acc tgc tta cct ggg aga ggg ctc ttc acc aat ggc tcc             1344
Asp Ile Tyr Thr Cys Leu Pro Gly Arg Gly Leu Phe Thr Asn Gly Ser
        435                 440                 445 tgt gca gac atc aag aaa gtt gag gcg tgg cag gtc ctg aag cac cta             1392
Cys Ala Asp Ile Lys Lys Val Glu Ala Trp Gln Val Leu Lys His Leu
    450                 455                 460 cgg cat cta aac ttt aca aac aat atg ggg gag cag gtg acc ttt gat             1440
Arg His Leu Asn Phe Thr Asn Asn Met Gly Glu Gln Val Thr Phe Asp
465                 470                 475                 480 gag tgt ggt gac ctg gtg ggg aac tat tcc atc atc aac tgg cac ctc             1488
Glu Cys Gly Asp Leu Val Gly Asn Tyr Ser Ile Ile Asn Trp His Leu
                485                 490                 495 tcc cca gag gat ggc tcc atc gtg ttt aag gaa gtc ggg tat tac aac             1536
Ser Pro Glu Asp Gly Ser Ile Val Phe Lys Glu Val Gly Tyr Tyr Asn
            500                 505                 510 gtc tat gcc aag aag gga gaa aga ctc ttc atc aac gag gag aaa atc             1584
Val Tyr Ala Lys Lys Gly Glu Arg Leu Phe Ile Asn Glu Glu Lys Ile
        515                 520                 525 ctg tgg agt ggg ttc tcc agg gag gtg ccc ttc tcc aac tgc agc cga             1632
Leu Trp Ser Gly Phe Ser Arg Glu Val Pro Phe Ser Asn Cys Ser Arg
    530                 535                 540 gac tgc ctg gca ggg acc agg aaa ggg atc att gag ggg gag ccc acc             1680
Asp Cys Leu Ala Gly Thr Arg Lys Gly Ile Ile Glu Gly Glu Pro Thr
545                 550                 555                 560 tgc tgc ttt gag tgt gtg gag tgt cct gat ggg gag tat agt gat gag             1728
```

-continued

| | | |
|---|---|---|
| Cys Cys Phe Glu Cys Val Glu Cys Pro Asp Gly Glu Tyr Ser Asp Glu<br>565 570 575 | | |
| aca gat gcc agt gcc tgt aac aag tgc cca gat gac ttc tgg tcc aat<br>Thr Asp Ala Ser Ala Cys Asn Lys Cys Pro Asp Asp Phe Trp Ser Asn<br>580 585 590 | 1776 | |
| gag aac cac acc tcc tgc gac ttg atc cca gta cag tat ctt cga tgg<br>Glu Asn His Thr Ser Cys Asp Leu Ile Pro Val Gln Tyr Leu Arg Trp<br>595 600 605 | 1824 | |
| ggt gac cct gaa ccc att gca gct gtg gtg ttt gcc tgc ctt ggc ctc<br>Gly Asp Pro Glu Pro Ile Ala Ala Val Val Phe Ala Cys Leu Gly Leu<br>610 615 620 | 1872 | |
| ctg gcc acc ctg ttt gtt act gta gtc ttc atc att tac cgt gat aca<br>Leu Ala Thr Leu Phe Val Thr Val Val Phe Ile Ile Tyr Arg Asp Thr<br>625 630 635 640 | 1920 | |
| cca gta gtc aag tcc tca agc agg gaa ctc tgc tac att atc ctt gct<br>Pro Val Val Lys Ser Ser Ser Arg Glu Leu Cys Tyr Ile Ile Leu Ala<br>645 650 655 | 1968 | |
| ggc atc tgc ctg ggc tac tta tgt acc ttc tgc ctc att gcg aag ccc<br>Gly Ile Cys Leu Gly Tyr Leu Cys Thr Phe Cys Leu Ile Ala Lys Pro<br>660 665 670 | 2016 | |
| aaa cag att tac tgc tac ctt cag aga att ggc att ggt ctc tcc cca<br>Lys Gln Ile Tyr Cys Tyr Leu Gln Arg Ile Gly Ile Gly Leu Ser Pro<br>675 680 685 | 2064 | |
| gcc atg agc tac tca gcc ctt gta aca aag acc aac cgt att gca agg<br>Ala Met Ser Tyr Ser Ala Leu Val Thr Lys Thr Asn Arg Ile Ala Arg<br>690 695 700 | 2112 | |
| atc ctg gct ggc agc aag aag aag atc tgt acc aaa aag ccc aga ttc<br>Ile Leu Ala Gly Ser Lys Lys Lys Ile Cys Thr Lys Lys Pro Arg Phe<br>705 710 715 720 | 2160 | |
| atg agt gcc tgt gcc cag cta gtg att gct ttc att ctc ata tgc atc<br>Met Ser Ala Cys Ala Gln Leu Val Ile Ala Phe Ile Leu Ile Cys Ile<br>725 730 735 | 2208 | |
| cag ttg ggc atc atc gtt gcc ctc ttt ata atg gag cct cct gac ata<br>Gln Leu Gly Ile Ile Val Ala Leu Phe Ile Met Glu Pro Pro Asp Ile<br>740 745 750 | 2256 | |
| atg cat gac tac cca agc att cga gaa gtc tac ctg atc tgt aac acc<br>Met His Asp Tyr Pro Ser Ile Arg Glu Val Tyr Leu Ile Cys Asn Thr<br>755 760 765 | 2304 | |
| acc aac cta gga gtt gtc act cca ctt gga tac aat gga ttg ttg att<br>Thr Asn Leu Gly Val Val Thr Pro Leu Gly Tyr Asn Gly Leu Leu Ile<br>770 775 780 | 2352 | |
| ttg agc tgc acc ttc tat gcg ttc aag acc aga aat gtt cca gct aac<br>Leu Ser Cys Thr Phe Tyr Ala Phe Lys Thr Arg Asn Val Pro Ala Asn<br>785 790 795 800 | 2400 | |
| ttc aac gag gcc aag tat atc gcc ttc aca atg tac acg acc tgc att<br>Phe Asn Glu Ala Lys Tyr Ile Ala Phe Thr Met Tyr Thr Thr Cys Ile<br>805 810 815 | 2448 | |
| ata tgg cta gct ttt gtg cca atc tac ttt ggc agc aac tac aaa atc<br>Ile Trp Leu Ala Phe Val Pro Ile Tyr Phe Gly Ser Asn Tyr Lys Ile<br>820 825 830 | 2496 | |
| atc acc atg tgt ttc tcg gtc agc ctc agt gcc aca gtg gcc cta ggc<br>Ile Thr Met Cys Phe Ser Val Ser Leu Ser Ala Thr Val Ala Leu Gly<br>835 840 845 | 2544 | |
| tgc atg ttt gtg ccg aag gtg tac atc atc ctg gcc aaa cca gag aga<br>Cys Met Phe Val Pro Lys Val Tyr Ile Ile Leu Ala Lys Pro Glu Arg<br>850 855 860 | 2592 | |
| aac gtg cgc agc gcc ttc acc aca tct acc gtg gtg cgc atg cat gta<br>Asn Val Arg Ser Ala Phe Thr Thr Ser Thr Val Val Arg Met His Val<br>865 870 875 880 | 2640 | |

-continued

```
ggg gat ggc aag tca tcc tcc gca gcc agc aga tcc agc agc cta gtc    2688
Gly Asp Gly Lys Ser Ser Ser Ala Ala Ser Arg Ser Ser Ser Leu Val
            885                 890                 895 aac ctg tgg aag aga agg ggc tcc tct ggg gaa acc tta agg tac aaa    2736
Asn Leu Trp Lys Arg Arg Gly Ser Ser Gly Glu Thr Leu Arg Tyr Lys
            900                 905                 910 gac agg aga ctg gcc cag cac aag tcg gaa ata gag tgt ttc acc ccg    2784
Asp Arg Arg Leu Ala Gln His Lys Ser Glu Ile Glu Cys Phe Thr Pro
            915                 920                 925 ccg tcc ccc ttc aga gac tcg gtg gac tcg ggg agc aca acc ccc aac    2832
Pro Ser Pro Phe Arg Asp Ser Val Asp Ser Gly Ser Thr Thr Pro Asn
        930                 935                 940 tcg cca gtg tcc gag tcg gcc ctc tgt atc ccg tcg tct ccc aaa tat    2880
Ser Pro Val Ser Glu Ser Ala Leu Cys Ile Pro Ser Ser Pro Lys Tyr
945                 950                 955                 960 gac act ctt atc ata aga gat tac act cag agc tcc tcg tcg ttg        2925
Asp Thr Leu Ile Ile Arg Asp Tyr Thr Gln Ser Ser Ser Ser Leu
                965                 970                 975

<210> SEQ ID NO 4
<211> LENGTH: 975
<212> TYPE: PRT
<213> ORGANISM: Artificial Sequence
<220> FEATURE:
<223> OTHER INFORMATION: Description of Artificial Sequence:Chimeric

<400> SEQUENCE: 4

Met Ala Phe Tyr Ser Cys Cys Trp Val Leu Leu Ala Leu Thr Trp His
1               5                   10                  15

Thr Ser Ala Tyr Gly Pro Asp Gln Arg Ala Gln Lys Lys Gly Asp Ile
            20                  25                  30

Ile Leu Gly Gly Leu Phe Pro Ile His Phe Gly Val Ala Ala Lys Asp
        35                  40                  45

Gln Asp Leu Lys Ser Arg Pro Glu Ser Val Glu Cys Ile Arg Tyr Asn
    50                  55                  60

Phe Arg Gly Phe Arg Trp Leu Gln Ala Met Ile Phe Ala Ile Glu Glu
65                  70                  75                  80

Ile Asn Ser Ser Pro Ala Leu Leu Pro Asn Leu Thr Leu Gly Tyr Arg
                85                  90                  95

Ile Phe Asp Thr Cys Asn Thr Val Ser Lys Ala Leu Glu Ala Thr Leu
            100                 105                 110

Ser Phe Val Ala Gln Asn Lys Ile Asp Ser Leu Asn Leu Asp Glu Phe
        115                 120                 125

Cys Asn Cys Ser Glu His Ile Pro Ser Thr Ile Ala Val Val Gly Ala
    130                 135                 140

Thr Gly Ser Gly Val Ser Thr Ala Val Ala Asn Leu Leu Gly Leu Phe
145                 150                 155                 160

Tyr Ile Pro Gln Val Ser Tyr Ala Ser Ser Arg Leu Leu Ser Asn
                165                 170                 175

Lys Asn Gln Phe Lys Ser Phe Leu Arg Thr Ile Pro Asn Asp Glu His
            180                 185                 190

Gln Ala Thr Ala Met Ala Asp Ile Ile Glu Tyr Phe Arg Trp Asn Trp
        195                 200                 205

Val Gly Thr Ile Ala Ala Asp Asp Asp Tyr Gly Arg Pro Gly Ile Glu
    210                 215                 220

Lys Phe Arg Glu Glu Ala Glu Glu Arg Asp Ile Cys Ile Asp Phe Ser
225                 230                 235                 240
```

```
Glu Leu Ile Ser Gln Tyr Ser Asp Glu Glu Ile Gln His Val Val
            245                 250                 255

Glu Val Ile Gln Asn Ser Thr Ala Lys Val Ile Val Phe Ser Ser
            260                 265                 270

Gly Pro Asp Leu Glu Pro Leu Ile Lys Glu Ile Val Arg Arg Asn Ile
            275                 280                 285

Thr Gly Lys Ile Trp Leu Ala Ser Glu Ala Trp Ala Ser Ser Ser Leu
290                 295                 300

Ile Ala Met Pro Gln Tyr Phe His Val Val Gly Thr Ile Gly Phe
305             310                 315                 320

Ala Leu Lys Ala Gly Gln Ile Pro Gly Phe Arg Glu Phe Leu Lys Lys
                325                 330                 335

Val His Pro Arg Lys Ser Val His Asn Gly Phe Ala Lys Glu Phe Trp
            340                 345                 350

Glu Glu Thr Phe Asn Cys His Leu Gln Glu Gly Ala Lys Gly Pro Leu
                355                 360                 365

Pro Val Asp Thr Phe Leu Arg Gly His Glu Glu Ser Gly Asp Arg Phe
            370                 375                 380

Ser Asn Ser Ser Thr Ala Phe Arg Pro Leu Cys Thr Gly Asp Glu Asn
385                 390                 395                 400

Ile Ser Ser Val Glu Thr Pro Tyr Ile Asp Tyr Thr His Leu Arg Ile
                405                 410                 415

Ser Tyr Asn Val Tyr Leu Ala Val Tyr Ser Ile Ala His Ala Leu Gln
            420                 425                 430

Asp Ile Tyr Thr Cys Leu Pro Gly Arg Gly Leu Phe Thr Asn Gly Ser
            435                 440                 445

Cys Ala Asp Ile Lys Lys Val Glu Ala Trp Gln Val Leu Lys His Leu
450                 455                 460

Arg His Leu Asn Phe Thr Asn Asn Met Gly Glu Gln Val Thr Phe Asp
465                 470                 475                 480

Glu Cys Gly Asp Leu Val Gly Asn Tyr Ser Ile Ile Asn Trp His Leu
                485                 490                 495

Ser Pro Glu Asp Gly Ser Ile Val Phe Lys Glu Val Gly Tyr Tyr Asn
            500                 505                 510

Val Tyr Ala Lys Lys Gly Glu Arg Leu Phe Ile Asn Glu Glu Lys Ile
            515                 520                 525

Leu Trp Ser Gly Phe Ser Arg Glu Val Pro Phe Ser Asn Cys Ser Arg
530                 535                 540

Asp Cys Leu Ala Gly Thr Arg Lys Gly Ile Ile Glu Gly Glu Pro Thr
545                 550                 555                 560

Cys Cys Phe Glu Cys Val Glu Cys Pro Asp Gly Glu Tyr Ser Asp Glu
                565                 570                 575

Thr Asp Ala Ser Ala Cys Asn Lys Cys Pro Asp Asp Phe Trp Ser Asn
            580                 585                 590

Glu Asn His Thr Ser Cys Asp Leu Ile Pro Val Gln Tyr Leu Arg Trp
            595                 600                 605

Gly Asp Pro Glu Pro Ile Ala Ala Val Phe Ala Cys Leu Gly Leu
            610                 615                 620

Leu Ala Thr Leu Phe Val Thr Val Val Phe Ile Ile Tyr Arg Asp Thr
625                 630                 635                 640

Pro Val Val Lys Ser Ser Ser Arg Glu Leu Cys Tyr Ile Ile Leu Ala
                645                 650                 655

Gly Ile Cys Leu Gly Tyr Leu Cys Thr Phe Cys Leu Ile Ala Lys Pro
```

-continued

```
                          660                 665                 670
Lys Gln Ile Tyr Cys Tyr Leu Gln Arg Ile Gly Ile Gly Leu Ser Pro
            675                 680                 685
Ala Met Ser Tyr Ser Ala Leu Val Thr Lys Thr Asn Arg Ile Ala Arg
    690                 695                 700
Ile Leu Ala Gly Ser Lys Lys Ile Cys Thr Lys Pro Arg Phe
705                 710                 715                 720
Met Ser Ala Cys Ala Gln Leu Val Ile Ala Phe Ile Leu Ile Cys Ile
                725                 730                 735
Gln Leu Gly Ile Ile Val Ala Leu Phe Ile Met Glu Pro Pro Asp Ile
            740                 745                 750
Met His Asp Tyr Pro Ser Ile Arg Glu Val Tyr Leu Ile Cys Asn Thr
            755                 760                 765
Thr Asn Leu Gly Val Val Thr Pro Leu Gly Tyr Asn Gly Leu Leu Ile
            770                 775                 780
Leu Ser Cys Thr Phe Tyr Ala Phe Lys Thr Arg Asn Val Pro Ala Asn
785                 790                 795                 800
Phe Asn Glu Ala Lys Tyr Ile Ala Phe Thr Met Tyr Thr Thr Cys Ile
                805                 810                 815
Ile Trp Leu Ala Phe Val Pro Ile Tyr Phe Gly Ser Asn Tyr Lys Ile
                820                 825                 830
Ile Thr Met Cys Phe Ser Val Ser Leu Ser Ala Thr Val Ala Leu Gly
            835                 840                 845
Cys Met Phe Val Pro Lys Val Tyr Ile Ile Leu Ala Lys Pro Glu Arg
    850                 855                 860
Asn Val Arg Ser Ala Phe Thr Thr Ser Thr Val Val Arg Met His Val
865                 870                 875                 880
Gly Asp Gly Lys Ser Ser Ala Ala Ser Arg Ser Ser Leu Val
                885                 890                 895
Asn Leu Trp Lys Arg Arg Gly Ser Ser Gly Glu Thr Leu Arg Tyr Lys
            900                 905                 910
Asp Arg Arg Leu Ala Gln His Lys Ser Glu Ile Glu Cys Phe Thr Pro
            915                 920                 925
Pro Ser Pro Phe Arg Asp Ser Val Asp Ser Gly Ser Thr Thr Pro Asn
    930                 935                 940
Ser Pro Val Ser Glu Ser Ala Leu Cys Ile Pro Ser Ser Pro Lys Tyr
945                 950                 955                 960
Asp Thr Leu Ile Ile Arg Asp Tyr Thr Gln Ser Ser Ser Ser Leu
                965                 970                 975
```

<210> SEQ ID NO 5
<211> LENGTH: 3129
<212> TYPE: DNA
<213> ORGANISM: Artificial Sequence
<220> FEATURE:
<223> OTHER INFORMATION: Description of Artificial Sequence:Chimeric
      molecule comprising portions of human mGluR5d and
      the human calcium receptor.
<220> FEATURE:
<221> NAME/KEY: CDS
<222> LOCATION: ()..(3129)

<400> SEQUENCE: 5

```
atg gtc ctt ctg ttg atc ctg tca gtc tta ctt ttg aaa gaa gat gtc      48
Met Val Leu Leu Leu Ile Leu Ser Val Leu Leu Leu Lys Glu Asp Val
  1               5                  10                  15 cgt ggg agt gca cag tcc agt gag agg agg gtg gtg gct cac atg ccg      96
```

-continued

```
          Arg Gly Ser Ala Gln Ser Ser Glu Arg Arg Val Val Ala His Met Pro
                       20                  25                  30 ggt gac atc att att gga gct ctc ttt tct gtt cat cac cag cct act        144
Gly Asp Ile Ile Ile Gly Ala Leu Phe Ser Val His His Gln Pro Thr
             35                  40                  45 gtg gac aaa gtt cat gag agg aag tgt ggg gcg gtc cgt gaa cag tat        192
Val Asp Lys Val His Glu Arg Lys Cys Gly Ala Val Arg Glu Gln Tyr
         50                  55                  60 ggc att cag aga gtg gag gcc atg ctg cat acc ctg gaa agg atc aat        240
Gly Ile Gln Arg Val Glu Ala Met Leu His Thr Leu Glu Arg Ile Asn
 65                  70                  75                  80 tca gac ccc aca ctc ttg ccc aac atc aca ctg ggc tgt gag ata agg        288
Ser Asp Pro Thr Leu Leu Pro Asn Ile Thr Leu Gly Cys Glu Ile Arg
                 85                  90                  95 gac tcc tgc tgg cat tcg gct gtg gcc cta gag cag agc att gag ttc        336
Asp Ser Cys Trp His Ser Ala Val Ala Leu Glu Gln Ser Ile Glu Phe
             100                 105                 110 ata aga gat tcc ctc att tct tca gaa gag gaa gaa ggc ttg gta cgc        384
Ile Arg Asp Ser Leu Ile Ser Ser Glu Glu Glu Glu Gly Leu Val Arg
         115                 120                 125 tgt gtg gat ggc tcc tcc tct tcc ttc cgc tcc aag aag ccc ata gta        432
Cys Val Asp Gly Ser Ser Ser Ser Phe Arg Ser Lys Lys Pro Ile Val
130                 135                 140 ggg gtc att ggg cct ggc tcc agt tct gta gcc att cag gtc cag aat        480
Gly Val Ile Gly Pro Gly Ser Ser Ser Val Ala Ile Gln Val Gln Asn
145                 150                 155                 160 ttg ctc cag ctt ttc aac ata cct cag att gct tac tca gca acc agc        528
Leu Leu Gln Leu Phe Asn Ile Pro Gln Ile Ala Tyr Ser Ala Thr Ser
                 165                 170                 175 atg gat ctg agt gac aag act ctg ttc aaa tat ttc atg agg gtt gtg        576
Met Asp Leu Ser Asp Lys Thr Leu Phe Lys Tyr Phe Met Arg Val Val
             180                 185                 190 cct tca gat gct cag cag gca agg gcc atg gtg gac ata gtg aag agg        624
Pro Ser Asp Ala Gln Gln Ala Arg Ala Met Val Asp Ile Val Lys Arg
         195                 200                 205 tac aac tgg acc tat gta tca gcc gtg cac aca gaa ggc aac tat gga        672
Tyr Asn Trp Thr Tyr Val Ser Ala Val His Thr Glu Gly Asn Tyr Gly
210                 215                 220 gaa agt ggg atg gaa gcc ttc aaa gat atg tca gcg aag gaa ggg att        720
Glu Ser Gly Met Glu Ala Phe Lys Asp Met Ser Ala Lys Glu Gly Ile
225                 230                 235                 240 tgc atc gcc cac tct tac aaa atc tac agt aat gca ggg gag cag agc        768
Cys Ile Ala His Ser Tyr Lys Ile Tyr Ser Asn Ala Gly Glu Gln Ser
                 245                 250                 255 ttt gat aag ctg ctg aag aag ctc aca agt cac ttg ccc aag gcc cgg        816
Phe Asp Lys Leu Leu Lys Lys Leu Thr Ser His Leu Pro Lys Ala Arg
             260                 265                 270 gtg gtg gcc tgc ttc tgt gag ggc atg acg gtg aga ggt ctg ctg atg        864
Val Val Ala Cys Phe Cys Glu Gly Met Thr Val Arg Gly Leu Leu Met
         275                 280                 285 gcc atg agg cgc ctg ggt cta gcg gga gaa ttt ctg ctt ctg ggc agt        912
Ala Met Arg Arg Leu Gly Leu Ala Gly Glu Phe Leu Leu Leu Gly Ser
290                 295                 300 gat ggc tgg gct gac agg tat gat gtg aca gat gga tat cag cga gaa        960
Asp Gly Trp Ala Asp Arg Tyr Asp Val Thr Asp Gly Tyr Gln Arg Glu
305                 310                 315                 320 gct gtt ggt ggc atc aca atc aag ctc caa tct ccc gat gtc aag tgg        1008
Ala Val Gly Gly Ile Thr Ile Lys Leu Gln Ser Pro Asp Val Lys Trp
                 325                 330                 335
```

```
ttt gat gat tat tat ctg aag ctc cgg cca gaa aca aac cac cga aac      1056
Phe Asp Asp Tyr Tyr Leu Lys Leu Arg Pro Glu Thr Asn His Arg Asn
            340                 345                 350 cct tgg ttt caa gaa ttt tgg cag cat cgt ttt cag tgc cga ctg gaa      1104
Pro Trp Phe Gln Glu Phe Trp Gln His Arg Phe Gln Cys Arg Leu Glu
    355                 360                 365 ggg ttt cca cag gag aac agc aaa tac aac aag act tgc aat agt tct      1152
Gly Phe Pro Gln Glu Asn Ser Lys Tyr Asn Lys Thr Cys Asn Ser Ser
370                 375                 380 ctg act ctg aaa aca cat cat gtt cag gat tcc aaa atg gga ttt gtg      1200
Leu Thr Leu Lys Thr His His Val Gln Asp Ser Lys Met Gly Phe Val
385                 390                 395                 400 atc aac gcc atc tat tcg atg gcc tat ggg ctc cac aac atg cag atg      1248
Ile Asn Ala Ile Tyr Ser Met Ala Tyr Gly Leu His Asn Met Gln Met
                405                 410                 415 tcc ctc tgc cca ggc tat gca gga ctc tgt gat gcc atg aag cca att      1296
Ser Leu Cys Pro Gly Tyr Ala Gly Leu Cys Asp Ala Met Lys Pro Ile
                420                 425                 430 gat gga cgg aaa ctt ttg gag tcc ctg atg aaa acc aat ttt act ggg      1344
Asp Gly Arg Lys Leu Leu Glu Ser Leu Met Lys Thr Asn Phe Thr Gly
            435                 440                 445 gtt tct gga gat acg atc cta ttc gat gag aat gga gac tct cca gga      1392
Val Ser Gly Asp Thr Ile Leu Phe Asp Glu Asn Gly Asp Ser Pro Gly
450                 455                 460 agg tat gaa ata atg aat ttc aag gaa atg gga aaa gat tac ttt gat      1440
Arg Tyr Glu Ile Met Asn Phe Lys Glu Met Gly Lys Asp Tyr Phe Asp
465                 470                 475                 480 tat atc aac gtt gga agt tgg gac aat gga gaa tta aaa atg gat gat      1488
Tyr Ile Asn Val Gly Ser Trp Asp Asn Gly Glu Leu Lys Met Asp Asp
                485                 490                 495 gat gaa gta tgg tcc aag aaa agc aac atc atc aga tct gtg tgc agt      1536
Asp Glu Val Trp Ser Lys Lys Ser Asn Ile Ile Arg Ser Val Cys Ser
                500                 505                 510 gaa cca tgt gag aaa ggc cag atc aag gtg atc cga aag gga gaa gtc      1584
Glu Pro Cys Glu Lys Gly Gln Ile Lys Val Ile Arg Lys Gly Glu Val
            515                 520                 525 agc tgt tgt tgg acc tgt aca cct tgt aag gag aat gag tat gtc ttt      1632
Ser Cys Cys Trp Thr Cys Thr Pro Cys Lys Glu Asn Glu Tyr Val Phe
530                 535                 540 gat gag tac aca tgc aag gca tgc caa ctg ggg tct tgg ccc act gat      1680
Asp Glu Tyr Thr Cys Lys Ala Cys Gln Leu Gly Ser Trp Pro Thr Asp
545                 550                 555                 560 gat ctc aca ggt tgt gac ttg atc cca gta cag tat ctt cga tgg ggt      1728
Asp Leu Thr Gly Cys Asp Leu Ile Pro Val Gln Tyr Leu Arg Trp Gly
                565                 570                 575 gac cct gaa ccc att gca gct gtg gtg ttt gcc tgc ctt ggc ctc ctg      1776
Asp Pro Glu Pro Ile Ala Ala Val Val Phe Ala Cys Leu Gly Leu Leu
                580                 585                 590 gcc acc ctg ttt gtt act gta gtc ttc atc att tac cgt gat aca cca      1824
Ala Thr Leu Phe Val Thr Val Val Phe Ile Ile Tyr Arg Asp Thr Pro
            595                 600                 605 gta gtc aag tcc tca agc agg gaa ctc tgc tac att atc ctt gct ggc      1872
Val Val Lys Ser Ser Ser Arg Glu Leu Cys Tyr Ile Ile Leu Ala Gly
            610                 615                 620 atc tgc ctg ggc tac tta tgt acc ttc tgc ctc att gcg aag ccc aaa      1920
Ile Cys Leu Gly Tyr Leu Cys Thr Phe Cys Leu Ile Ala Lys Pro Lys
625                 630                 635                 640 cag att tac tgc tac ctt cag aga att ggc att ggt ctc tcc cca gcc      1968
Gln Ile Tyr Cys Tyr Leu Gln Arg Ile Gly Ile Gly Leu Ser Pro Ala
                645                 650                 655
```

```
atg agc tac tca gcc ctt gta aca aag acc aac cgt att gca agg atc      2016
Met Ser Tyr Ser Ala Leu Val Thr Lys Thr Asn Arg Ile Ala Arg Ile
            660                 665                 670 ctg gct ggc agc aag aag aag atc tgt acc aaa aag ccc aga ttc atg      2064
Leu Ala Gly Ser Lys Lys Lys Ile Cys Thr Lys Lys Pro Arg Phe Met
        675                 680                 685 agt gcc tgt gcc cag cta gtg att gct ttc att ctc ata tgc atc cag      2112
Ser Ala Cys Ala Gln Leu Val Ile Ala Phe Ile Leu Ile Cys Ile Gln
    690                 695                 700 ttg ggc atc atc gtt gcc ctc ttt ata atg gag cct cct gac ata atg      2160
Leu Gly Ile Ile Val Ala Leu Phe Ile Met Glu Pro Pro Asp Ile Met
705                 710                 715                 720 cat gac tac cca agc att cga gaa gtc tac ctg atc tgt aac acc acc      2208
His Asp Tyr Pro Ser Ile Arg Glu Val Tyr Leu Ile Cys Asn Thr Thr
                725                 730                 735 aac cta gga gtt gtc act cca ctt gga tac aat gga ttg ttg att ttg      2256
Asn Leu Gly Val Val Thr Pro Leu Gly Tyr Asn Gly Leu Leu Ile Leu
            740                 745                 750 agc tgc acc ttc tat gcg ttc aag acc aga aat gtt cca gct aac ttc      2304
Ser Cys Thr Phe Tyr Ala Phe Lys Thr Arg Asn Val Pro Ala Asn Phe
        755                 760                 765 aac gag gcc aag tat atc gcc ttc aca atg tac acg acc tgc att ata      2352
Asn Glu Ala Lys Tyr Ile Ala Phe Thr Met Tyr Thr Thr Cys Ile Ile
    770                 775                 780 tgg cta gct ttt gtg cca atc tac ttt ggc agc aac tac aaa atc atc      2400
Trp Leu Ala Phe Val Pro Ile Tyr Phe Gly Ser Asn Tyr Lys Ile Ile
785                 790                 795                 800 acc atg tgt ttc tcg gtc agc ctc agt gcc aca gtg gcc cta ggc tgc      2448
Thr Met Cys Phe Ser Val Ser Leu Ser Ala Thr Val Ala Leu Gly Cys
                805                 810                 815 atg ttt gtg ccg aag gtg tac atc atc ctg gcc aaa cca gag aga aac      2496
Met Phe Val Pro Lys Val Tyr Ile Ile Leu Ala Lys Pro Glu Arg Asn
            820                 825                 830 gtg cgc agc gag gtg cgt tgc agc acc gca gct cac gct ttc aag gtg      2544
Val Arg Ser Glu Val Arg Cys Ser Thr Ala Ala His Ala Phe Lys Val
        835                 840                 845 gct gcc cgg gcc acg ctg cgc cgc agc aac gtc tcc cgc aag cgg tcc      2592
Ala Ala Arg Ala Thr Leu Arg Arg Ser Asn Val Ser Arg Lys Arg Ser
    850                 855                 860 agc agc ctt gga ggc tcc acg gga tcc acc ccc tcc tcc atc agc          2640
Ser Ser Leu Gly Gly Ser Thr Gly Ser Thr Pro Ser Ser Ile Ser
865                 870                 875                 880 agc aag agc aac agc gaa gac cca ttc cca cag ccc gag agg cag aag      2688
Ser Lys Ser Asn Ser Glu Asp Pro Phe Pro Gln Pro Glu Arg Gln Lys
                885                 890                 895 cag cag cag ccg ctg gcc cta acc cag caa gag cag cag cag cag ccc      2736
Gln Gln Gln Pro Leu Ala Leu Thr Gln Gln Glu Gln Gln Gln Gln Pro
            900                 905                 910 ctg acc ctc cca cag cag caa cga tct cag cag cag ccc aga tgc aag      2784
Leu Thr Leu Pro Gln Gln Gln Arg Ser Gln Gln Gln Pro Arg Cys Lys
        915                 920                 925 cag aag gtc atc ttt ggc agc ggc acg gtc acc ttc tca ctg agc ttt      2832
Gln Lys Val Ile Phe Gly Ser Gly Thr Val Thr Phe Ser Leu Ser Phe
    930                 935                 940 gat gag cct cag aag aac gcc atg gcc cac ggg aat tct acg cac cag      2880
Asp Glu Pro Gln Lys Asn Ala Met Ala His Gly Asn Ser Thr His Gln
945                 950                 955                 960 aac tcc ctg gag gcc cag aaa agc agc gat acg ctg acc cga cac cag      2928
Asn Ser Leu Glu Ala Gln Lys Ser Ser Asp Thr Leu Thr Arg His Gln
```

|  |  |
|---|---|
| cca tta ctc ccg ctg cag tgc ggg gaa acg gac tta gat ctg acc gtc<br>Pro Leu Leu Pro Leu Gln Cys Gly Glu Thr Asp Leu Asp Leu Thr Val<br>        980                     985                    990 | 2976 |
| cag gaa aca ggt ctg caa gga cct gtg ggt gga gac cag cgg cca gag<br>Gln Glu Thr Gly Leu Gln Gly Pro Val Gly Gly Asp Gln Arg Pro Glu<br>     995                     1000                    1005 | 3024 |
| gtg gag gac cct gaa gag ttg tcc cca gca ctt gta gtg tcc agt tca<br>Val Glu Asp Pro Glu Glu Leu Ser Pro Ala Leu Val Val Ser Ser Ser<br>1010                   1015                   1020 | 3072 |
| cag agc ttt gtc atc agt ggt gga ggc agc act gtt aca gaa aac gta<br>Gln Ser Phe Val Ile Ser Gly Gly Gly Ser Thr Val Thr Glu Asn Val<br>1025                   1030                   1035                  1040 | 3120 |
| gtg aat tca<br>Val Asn Ser | 3129 |

<210> SEQ ID NO 6
<211> LENGTH: 1043
<212> TYPE: PRT
<213> ORGANISM: Artificial Sequence
<220> FEATURE:
<223> OTHER INFORMATION: Description of Artificial Sequence:Chimeric

<400> SEQUENCE: 6

```
Met Val Leu Leu Ile Leu Ser Val Leu Leu Lys Glu Asp Val
  1               5                  10                  15

Arg Gly Ser Ala Gln Ser Ser Glu Arg Val Val Ala His Met Pro
                 20                  25                  30

Gly Asp Ile Ile Ile Gly Ala Leu Phe Ser Val His His Gln Pro Thr
             35                  40                  45

Val Asp Lys Val His Glu Arg Lys Cys Gly Ala Val Arg Glu Gln Tyr
 50                  55                  60

Gly Ile Gln Arg Val Glu Ala Met Leu His Thr Leu Glu Arg Ile Asn
 65                  70                  75                  80

Ser Asp Pro Thr Leu Leu Pro Asn Ile Thr Leu Gly Cys Glu Ile Arg
                 85                  90                  95

Asp Ser Cys Trp His Ser Ala Val Ala Leu Glu Gln Ser Ile Glu Phe
            100                 105                 110

Ile Arg Asp Ser Leu Ile Ser Ser Glu Glu Glu Glu Gly Leu Val Arg
        115                 120                 125

Cys Val Asp Gly Ser Ser Ser Phe Arg Ser Lys Lys Pro Ile Val
    130                 135                 140

Gly Val Ile Gly Pro Gly Ser Ser Ser Val Ala Ile Gln Val Gln Asn
145                 150                 155                 160

Leu Leu Gln Leu Phe Asn Ile Pro Gln Ile Ala Tyr Ser Ala Thr Ser
                165                 170                 175

Met Asp Leu Ser Asp Lys Thr Leu Phe Lys Tyr Phe Met Arg Val Val
            180                 185                 190

Pro Ser Asp Ala Gln Gln Ala Arg Ala Met Val Asp Ile Val Lys Arg
        195                 200                 205

Tyr Asn Trp Thr Tyr Val Ser Ala Val His Thr Glu Gly Asn Tyr Gly
    210                 215                 220

Glu Ser Gly Met Glu Ala Phe Lys Asp Met Ser Ala Lys Glu Gly Ile
225                 230                 235                 240

Cys Ile Ala His Ser Tyr Lys Ile Tyr Ser Asn Ala Gly Glu Gln Ser
                245                 250                 255
```

```
Phe Asp Lys Leu Leu Lys Lys Leu Thr Ser His Leu Pro Lys Ala Arg
            260                 265                 270

Val Val Ala Cys Phe Cys Glu Gly Met Thr Val Arg Gly Leu Leu Met
            275                 280                 285

Ala Met Arg Arg Leu Gly Leu Ala Gly Glu Phe Leu Leu Leu Gly Ser
            290                 295                 300

Asp Gly Trp Ala Asp Arg Tyr Asp Val Thr Asp Gly Tyr Gln Arg Glu
305                 310                 315                 320

Ala Val Gly Gly Ile Thr Ile Lys Leu Gln Ser Pro Asp Val Lys Trp
                325                 330                 335

Phe Asp Asp Tyr Tyr Leu Lys Leu Arg Pro Glu Thr Asn His Arg Asn
            340                 345                 350

Pro Trp Phe Gln Glu Phe Trp Gln His Arg Phe Gln Cys Arg Leu Glu
            355                 360                 365

Gly Phe Pro Gln Glu Asn Ser Lys Tyr Asn Lys Thr Cys Asn Ser Ser
            370                 375                 380

Leu Thr Leu Lys Thr His His Val Gln Asp Ser Lys Met Gly Phe Val
385                 390                 395                 400

Ile Asn Ala Ile Tyr Ser Met Ala Tyr Gly Leu His Asn Met Gln Met
                405                 410                 415

Ser Leu Cys Pro Gly Tyr Ala Gly Leu Cys Asp Ala Met Lys Pro Ile
            420                 425                 430

Asp Gly Arg Lys Leu Leu Glu Ser Leu Met Lys Thr Asn Phe Thr Gly
            435                 440                 445

Val Ser Gly Asp Thr Ile Leu Phe Asp Glu Asn Gly Asp Ser Pro Gly
            450                 455                 460

Arg Tyr Glu Ile Met Asn Phe Lys Glu Met Gly Lys Asp Tyr Phe Asp
465                 470                 475                 480

Tyr Ile Asn Val Gly Ser Trp Asp Asn Gly Glu Leu Lys Met Asp Asp
                485                 490                 495

Asp Glu Val Trp Ser Lys Lys Ser Asn Ile Ile Arg Ser Val Cys Ser
            500                 505                 510

Glu Pro Cys Glu Lys Gly Gln Ile Lys Val Ile Arg Lys Gly Glu Val
            515                 520                 525

Ser Cys Cys Trp Thr Cys Thr Pro Cys Lys Glu Asn Glu Tyr Val Phe
            530                 535                 540

Asp Glu Tyr Thr Cys Lys Ala Cys Gln Leu Gly Ser Trp Pro Thr Asp
545                 550                 555                 560

Asp Leu Thr Gly Cys Asp Leu Ile Pro Val Gln Tyr Leu Arg Trp Gly
                565                 570                 575

Asp Pro Glu Pro Ile Ala Ala Val Val Phe Ala Cys Leu Gly Leu Leu
            580                 585                 590

Ala Thr Leu Phe Val Thr Val Phe Ile Ile Tyr Arg Asp Thr Pro
            595                 600                 605

Val Val Lys Ser Ser Ser Arg Glu Leu Cys Tyr Ile Ile Leu Ala Gly
            610                 615                 620

Ile Cys Leu Gly Tyr Leu Cys Thr Phe Cys Leu Ile Ala Lys Pro Lys
625                 630                 635                 640

Gln Ile Tyr Cys Tyr Leu Gln Arg Ile Gly Ile Gly Leu Ser Pro Ala
                645                 650                 655

Met Ser Tyr Ser Ala Leu Val Thr Lys Thr Asn Arg Ile Ala Arg Ile
            660                 665                 670
```

Leu Ala Gly Ser Lys Lys Ile Cys Thr Lys Lys Pro Arg Phe Met
    675                 680                 685

Ser Ala Cys Ala Gln Leu Val Ile Ala Phe Ile Leu Ile Cys Ile Gln
    690                 695                 700

Leu Gly Ile Ile Val Ala Leu Phe Ile Met Glu Pro Pro Asp Ile Met
705                 710                 715                 720

His Asp Tyr Pro Ser Ile Arg Glu Val Tyr Leu Ile Cys Asn Thr Thr
                725                 730                 735

Asn Leu Gly Val Val Thr Pro Leu Gly Tyr Asn Gly Leu Leu Ile Leu
            740                 745                 750

Ser Cys Thr Phe Tyr Ala Phe Lys Thr Arg Asn Val Pro Ala Asn Phe
        755                 760                 765

Asn Glu Ala Lys Tyr Ile Ala Phe Thr Met Tyr Thr Thr Cys Ile Ile
    770                 775                 780

Trp Leu Ala Phe Val Pro Ile Tyr Phe Gly Ser Asn Tyr Lys Ile Ile
785                 790                 795                 800

Thr Met Cys Phe Ser Val Ser Leu Ser Ala Thr Val Ala Leu Gly Cys
                805                 810                 815

Met Phe Val Pro Lys Val Tyr Ile Ile Leu Ala Lys Pro Glu Arg Asn
            820                 825                 830

Val Arg Ser Glu Val Arg Cys Ser Thr Ala Ala His Ala Phe Lys Val
        835                 840                 845

Ala Ala Arg Ala Thr Leu Arg Arg Ser Asn Val Ser Arg Lys Arg Ser
    850                 855                 860

Ser Ser Leu Gly Gly Ser Thr Gly Ser Thr Pro Ser Ser Ser Ile Ser
865                 870                 875                 880

Ser Lys Ser Asn Ser Glu Asp Pro Phe Pro Gln Pro Glu Arg Gln Lys
                885                 890                 895

Gln Gln Gln Pro Leu Ala Leu Thr Gln Gln Glu Gln Gln Gln Gln Pro
            900                 905                 910

Leu Thr Leu Pro Gln Gln Gln Arg Ser Gln Gln Gln Pro Arg Cys Lys
        915                 920                 925

Gln Lys Val Ile Phe Gly Ser Gly Thr Val Thr Phe Ser Leu Ser Phe
    930                 935                 940

Asp Glu Pro Gln Lys Asn Ala Met Ala His Gly Asn Ser Thr His Gln
945                 950                 955                 960

Asn Ser Leu Glu Ala Gln Lys Ser Ser Asp Thr Leu Thr Arg His Gln
                965                 970                 975

Pro Leu Leu Pro Leu Gln Cys Gly Glu Thr Asp Leu Asp Leu Thr Val
            980                 985                 990

Gln Glu Thr Gly Leu Gln Gly Pro Val Gly Gly Asp Gln Arg Pro Glu
        995                 1000                1005

Val Glu Asp Pro Glu Glu Leu Ser Pro Ala Leu Val Val Ser Ser Ser
    1010                1015                1020

Gln Ser Phe Val Ile Ser Gly Gly Gly Ser Thr Val Thr Glu Asn Val
1025                1030                1035                1040

Val Asn Ser

<210> SEQ ID NO 7
<211> LENGTH: 1212
<212> TYPE: PRT
<213> ORGANISM: Homo sapiens

<400> SEQUENCE: 7

-continued

```
Met Val Leu Leu Leu Ile Leu Ser Val Leu Leu Lys Glu Asp Val
 1               5                  10                  15

Arg Gly Ser Ala Gln Ser Glu Arg Arg Val Ala His Met Pro
                 20                  25                  30

Gly Asp Ile Ile Ile Gly Ala Leu Phe Ser Val His His Gln Pro Thr
                 35                  40                  45

Val Asp Lys Val His Glu Arg Lys Cys Gly Ala Val Arg Glu Gln Tyr
     50                  55                  60

Gly Ile Gln Arg Val Glu Ala Met Leu His Thr Leu Glu Arg Ile Asn
 65                  70                  75                  80

Ser Asp Pro Thr Leu Leu Pro Asn Ile Thr Leu Gly Cys Glu Ile Arg
                 85                  90                  95

Asp Ser Cys Trp His Ser Ala Val Ala Leu Glu Gln Ser Ile Glu Phe
                100                 105                 110

Ile Arg Asp Ser Leu Ile Ser Ser Glu Glu Glu Gly Leu Val Arg
                115                 120                 125

Cys Val Asp Gly Ser Ser Ser Phe Arg Ser Lys Lys Pro Ile Val
    130                 135                 140

Gly Val Ile Gly Pro Gly Ser Ser Val Ala Ile Gln Val Gln Asn
145                 150                 155                 160

Leu Leu Gln Leu Phe Asn Ile Pro Gln Ile Ala Tyr Ser Ala Thr Ser
                165                 170                 175

Met Asp Leu Ser Asp Lys Thr Leu Phe Lys Tyr Phe Met Arg Val Val
                180                 185                 190

Pro Ser Asp Ala Gln Gln Ala Arg Ala Met Val Asp Ile Val Lys Arg
    195                 200                 205

Tyr Asn Trp Thr Tyr Val Ser Ala Val His Thr Glu Gly Asn Tyr Gly
210                 215                 220

Glu Ser Gly Met Glu Ala Phe Lys Asp Met Ser Ala Lys Glu Gly Ile
225                 230                 235                 240

Cys Ile Ala His Ser Tyr Lys Ile Tyr Ser Asn Ala Gly Glu Gln Ser
                245                 250                 255

Phe Asp Lys Leu Leu Lys Lys Leu Thr Ser His Leu Pro Lys Ala Arg
    260                 265                 270

Val Val Ala Cys Phe Cys Glu Gly Met Thr Val Arg Gly Leu Leu Met
    275                 280                 285

Ala Met Arg Arg Leu Gly Leu Ala Gly Glu Phe Leu Leu Leu Gly Ser
    290                 295                 300

Asp Gly Trp Ala Asp Arg Tyr Asp Val Thr Asp Gly Tyr Gln Arg Glu
305                 310                 315                 320

Ala Val Gly Gly Ile Thr Ile Lys Leu Gln Ser Pro Asp Val Lys Trp
                325                 330                 335

Phe Asp Asp Tyr Tyr Leu Lys Leu Arg Pro Glu Thr Asn His Arg Asn
                340                 345                 350

Pro Trp Phe Gln Glu Phe Trp Gln His Arg Phe Gln Cys Arg Leu Glu
    355                 360                 365

Gly Phe Pro Gln Glu Asn Ser Lys Tyr Asn Lys Thr Cys Asn Ser Ser
    370                 375                 380

Leu Thr Leu Lys Thr His His Val Gln Asp Ser Lys Met Gly Phe Val
385                 390                 395                 400

Ile Asn Ala Ile Tyr Ser Met Ala Tyr Gly Leu His Asn Met Gln Met
                405                 410                 415

Ser Leu Cys Pro Gly Tyr Ala Gly Leu Cys Asp Ala Met Lys Pro Ile
```

-continued

```
                420             425             430
Asp Gly Arg Lys Leu Leu Glu Ser Leu Met Lys Thr Asn Phe Thr Gly
            435                 440                 445
Val Ser Gly Asp Thr Ile Leu Phe Asp Glu Asn Gly Asp Ser Pro Gly
            450                 455                 460
Arg Tyr Glu Ile Met Asn Phe Lys Glu Met Gly Lys Asp Tyr Phe Asp
465                 470                 475                 480
Tyr Ile Asn Val Gly Ser Trp Asp Asn Gly Glu Leu Lys Met Asp Asp
                    485                 490                 495
Asp Glu Val Trp Ser Lys Lys Ser Asn Ile Ile Arg Ser Val Cys Ser
                500                 505                 510
Glu Pro Cys Glu Lys Gly Gln Ile Lys Val Ile Arg Lys Gly Glu Val
            515                 520                 525
Ser Cys Cys Trp Thr Cys Thr Pro Cys Lys Glu Asn Glu Tyr Val Phe
            530                 535                 540
Asp Glu Tyr Thr Cys Lys Ala Cys Gln Leu Gly Ser Trp Pro Thr Asp
545                 550                 555                 560
Asp Leu Thr Gly Cys Asp Leu Ile Pro Val Gln Tyr Leu Arg Trp Gly
                    565                 570                 575
Asp Pro Glu Pro Ile Ala Ala Val Val Phe Ala Cys Leu Gly Leu Leu
                580                 585                 590
Ala Thr Leu Phe Val Thr Val Val Phe Ile Ile Tyr Arg Asp Thr Pro
            595                 600                 605
Val Val Lys Ser Ser Ser Arg Glu Leu Cys Tyr Ile Ile Leu Ala Gly
            610                 615                 620
Ile Cys Leu Gly Tyr Leu Cys Thr Phe Cys Leu Ile Ala Lys Pro Lys
625                 630                 635                 640
Gln Ile Tyr Cys Tyr Leu Gln Arg Ile Gly Ile Gly Leu Ser Pro Ala
                    645                 650                 655
Met Ser Tyr Ser Ala Leu Val Thr Lys Thr Asn Arg Ile Ala Arg Ile
                660                 665                 670
Leu Ala Gly Ser Lys Lys Lys Ile Cys Thr Lys Lys Pro Arg Phe Met
            675                 680                 685
Ser Ala Cys Ala Gln Leu Val Ile Ala Phe Ile Leu Ile Cys Ile Gln
            690                 695                 700
Leu Gly Ile Ile Val Ala Leu Phe Ile Met Glu Pro Pro Asp Ile Met
705                 710                 715                 720
His Asp Tyr Pro Ser Ile Arg Glu Val Tyr Leu Ile Cys Asn Thr Thr
                    725                 730                 735
Asn Leu Gly Val Val Thr Pro Leu Gly Tyr Asn Gly Leu Leu Ile Leu
                740                 745                 750
Ser Cys Thr Phe Tyr Ala Phe Lys Thr Arg Asn Val Pro Ala Asn Phe
            755                 760                 765
Asn Glu Ala Lys Tyr Ile Ala Phe Thr Met Tyr Thr Thr Cys Ile Ile
            770                 775                 780
Trp Leu Ala Phe Val Pro Ile Tyr Phe Gly Ser Asn Tyr Lys Ile Ile
785                 790                 795                 800
Thr Met Cys Phe Ser Val Ser Leu Ser Ala Thr Val Ala Leu Gly Cys
                    805                 810                 815
Met Phe Val Pro Lys Val Tyr Ile Ile Leu Ala Lys Pro Glu Arg Asn
                820                 825                 830
Val Arg Ser Ala Phe Thr Thr Ser Thr Val Val Arg Met His Val Gly
            835                 840                 845
```

-continued

```
Asp Gly Lys Ser Ser Ala Ala Ser Arg Ser Ser Leu Val Asn
    850                 855                 860

Leu Trp Lys Arg Arg Gly Ser Ser Gly Glu Thr Leu Arg Tyr Lys Asp
865                 870                 875                 880

Arg Arg Leu Ala Gln His Lys Ser Glu Ile Glu Cys Phe Thr Pro Lys
                885                 890                 895

Gly Ser Met Gly Asn Gly Gly Arg Ala Thr Met Ser Ser Asn Gly
            900                 905                 910

Lys Ser Val Thr Trp Ala Gln Asn Glu Lys Ser Ser Arg Gly Gln His
        915                 920                 925

Leu Trp Gln Arg Leu Ser Ile His Ile Asn Lys Lys Glu Asn Pro Asn
    930                 935                 940

Gln Thr Ala Val Ile Lys Pro Phe Pro Lys Ser Thr Glu Ser Arg Gly
945                 950                 955                 960

Leu Gly Ala Gly Ala Gly Ala Gly Gly Ser Ala Gly Gly Val Gly Ala
                965                 970                 975

Thr Gly Gly Ala Gly Cys Ala Gly Ala Gly Pro Gly Gly Pro Glu Ser
            980                 985                 990

Pro Asp Ala Gly Pro Lys Ala Leu Tyr Asp Val Ala Glu Ala Glu Glu
        995                 1000                1005

His Phe Pro Ala Pro Ala Arg Pro Arg Ser Pro Ser Pro Ile Ser Thr
    1010                1015                1020

Leu Ser His Arg Ala Gly Ser Ala Ser Arg Thr Asp Asp Val Pro
1025                1030                1035                1040

Ser Leu His Ser Glu Pro Val Ala Arg Ser Ser Ser Gln Gly Ser
                1045                1050                1055

Leu Met Glu Gln Ile Ser Ser Val Val Thr Arg Phe Thr Ala Asn Ile
            1060                1065                1070

Ser Glu Leu Asn Ser Met Met Leu Ser Thr Ala Ala Pro Ser Pro Gly
        1075                1080                1085

Val Gly Ala Pro Leu Cys Ser Ser Tyr Leu Ile Pro Lys Glu Ile Gln
    1090                1095                1100

Leu Pro Thr Thr Met Thr Thr Phe Ala Glu Ile Gln Pro Leu Pro Ala
1105                1110                1115                1120

Ile Glu Val Thr Gly Gly Ala Gln Pro Ala Ala Gly Ala Gln Ala Ala
                1125                1130                1135

Gly Asp Ala Ala Arg Glu Ser Pro Ala Ala Gly Pro Glu Ala Ala Ala
            1140                1145                1150

Ala Lys Pro Asp Leu Glu Glu Leu Val Ala Leu Thr Pro Pro Ser Pro
        1155                1160                1165

Phe Arg Asp Ser Val Asp Ser Gly Ser Thr Pro Asn Ser Pro Val
    1170                1175                1180

Ser Glu Ser Ala Leu Cys Ile Pro Ser Ser Pro Lys Tyr Asp Thr Leu
1185                1190                1195                1200

Ile Ile Arg Asp Tyr Thr Gln Ser Ser Ser Ser Leu
                1205                1210
```

HUMAN METABOTROPIC GLUTAMATE RECEPTOR

1. RELATED APPLICATIONS

This application is related to and claims the benefit of U.S. Provisional Application Ser. No. 60/161,481 of Thomas M. Stormann, Laura Storjohann, Cynthia Levinthal, Lance G. Hammerland, and Karen J. Krapcho filed Oct. 25, 1999 and entitled "A Novel Human Metabotropic Receptor," and U.S. Utility patent application Ser. No. 09/695,481, filed Oct. 24, 2000, of Thomas M. Stormann, Laura Storjohann, Cynthia Levinthal, Lance G. Hammerland, and Karen J. Krapcho, now U.S. Pat. No. 6,534,287, issued Mar. 18, 2003, which are incorporated herein by this reference.

2. FIELD OF THE INVENTION

The present invention relates to nucleic acid sequences coding for a newly identified splice variant of human metabotropic glutamate receptor 5 (mGluR5). The novel human receptor may be expressed in host cells which may be used to screen for agonist, antagonist, and modulatory molecules that act on the novel human mGluR5. These molecules acting on the novel human mGluR can be used to modulate the activity of the novel human receptor for the treatment of neurological disorders and diseases.

The invention also relates to nucleic acids encoding such receptors, genetically modified cells containing such nucleic acids, methods of screening for compounds that bind to or modulate the activity of such receptors, and methods of use relating to all of the foregoing.

3. BACKGROUND OF THE INVENTION

The following description provides a summary of information related to the background of the present invention. It is not an admission that any of the information provided herein is prior art to the presently claimed invention, nor that any of the publications specifically or implicitly referenced are prior art to that invention.

Glutamate is the major excitatory neurotransmitter in the mammalian central nervous system (CNS). Glutamate produces its effects on central neurons by binding to and thereby activating cell surface receptors. These receptors have been subdivided into two major classes, the ionotropic and metabotropic glutamate receptors, based on the structural features of the receptor proteins, the means by which the receptors transduce signals into the cell, and pharmacological profiles.

The ionotropic glutamate receptors (iGluRs) are ligand-gated ion channels that, upon binding glutamate, open to allow the selective influx of certain monovalent and divalent cations, thereby depolarizing the cell membrane. In addition, certain iGluRs with relatively high calcium permeability can activate a variety of calcium-dependent intracellular processes. These receptors are multisubunit protein complexes that may be homomeric or heteromeric in nature. The various iGluR subunits all share common structural motifs, including a relatively large amino-terminal extracellular domain (ECD), followed by two transmembrane domains (TMD), a second smaller extracellular domain, and a third TMD, before terminating with an intracellular carboxy-terminal domain. Historically, the iGluRs were first subdivided pharmacologically into three classes based on preferential activation by the agonists α-amino-3-hydroxy-5-methylisoxazole-4-propionic acid (AMPA), kainate (KA), and N-methyl-D-aspartate (NMDA). Later, molecular cloning studies coupled with additional pharmacological studies revealed a greater diversity of iGluRs, in that multiple subtypes of AMPA, KA and NMDA receptors are expressed in the mammalian CNS. Hollman & Heinemann (1994), *Ann. Rev. Neurosci.* 17:31.

The metabotropic glutamate receptors (mGluRs) are G-protein-coupled receptors capable of activating a variety of intracellular second messenger systems following the binding of glutamate. Activation of mGluRs in intact mammalian neurons can elicit one or more of the following responses: activation of phospholipase C, increases in phosphoinositide (PI) hydrolysis, intracellular calcium release, activation of phospholipase D, activation or inhibition of adenylyl cyclase, increases or decreases in the formation of cyclic adenosine monophosphate (cAMP), activation of guanylyl cyclase, increases in the formation of cyclic guanosine monophosphate (cGMP), activation of phospholipase $A_2$, increases in arachidonic acid release, and increases or decreases in the activity of ion channels (e.g., voltage- and ligand-gated ion channels). Schoepp & Conn (1993), *Trends Pharmacol. Sci.* 14:13; Schoepp (1994), *Neurochem. Int.* 24:439; Pin & Duvoisin (1995), *Neuropharmacology* 34:1.

Thus far, eight distinct mGluR subtypes have been isolated via molecular cloning, and named mGluR1 to mGluR8 according to the order in which they were discovered. Nakanishi (1994), *Neuron* 13:1031; Pin & Duvoisin (1995), *Neuropharmacology* 34:1; Knopfel et al. (1995), *J. Med. Chem.* 38:1417. Further diversity occurs through the expression of alternatively spliced forms of certain mGluR subtypes. Pin et al. (1992), *Proc. Natl. Acad. Sci. USA* 89:10331; Minakami et al. (1994), *BBRC* 199:1136; Joly et al. (1995), *J. Neurosci.* 15:3970. All of the mGluRs are structurally similar, in that they are single subunit membrane proteins possessing a large amino-terminal ECD, followed by seven putative TMDs, and an intracellular carboxy-terminal domain of variable length.

The eight mGluRs have been subdivided into three groups based on amino acid sequence homologies, the second messenger systems they utilize, and pharmacological characteristics. Nakanishi (1994), *Neuron* 13:1031; Pin & Duvoisin (1995), *Neuropharmacology* 34:1; Knopfel et al. (1995), *J. Med. Chem.* 38:1417. The amino acid homology between mGluRs within a given group is approximately 70%, but drops to about 40% between mGluRs in different groups. For mGluRs in the same group, this relatedness is roughly paralleled by similarities in signal transduction mechanisms and pharmacological characteristics.

The Group I mGluRs comprise mGluR1, mGluR5, and their alternatively spliced variants. The binding of agonists to these receptors results in the activation of phospholipase C and the subsequent mobilization of intracellular calcium. For example, *Xenopus* oocytes expressing recombinant mGluR1 receptors have been utilized to demonstrate this effect indirectly by electrophysiological means. Masu et al. (1991), *Nature* 349:760; Pin et al. (1992), *Proc. Natl. Acad. Sci. USA* 89:10331. Similar results were achieved with oocytes expressing recombinant mGluR5 receptors. Abe et al. (1992), *J. Biol. Chem.* 267:13361; Minakami et al. (1994), *BBRC* 199:1136; Joly et al. (1995), *J. Neurosci.* 15:3970. Alternatively, agonist activation of recombinant mGluR1 receptors expressed in Chinese hamster ovary (CHO) cells stimulated PI hydrolysis, cAMP formation, and arachidonic acid release as measured by standard biochemical assays. Aramori & Nakanishi (1992), *Neuron* 8:757. In comparison, activation of mGluR5 receptors expressed in CHO cells stimulated PI hydrolysis and subsequent intracellular calcium transients, but no stimulation of cAMP formation or arachidonic acid release was observed. Abe et al. (1992), *J. Biol. Chem.* 267:13361. However, activation of mGluR5 receptors expressed in LLC-PK1 cells does result in increased cAMP formation as well as PI hydrolysis. Joly et al. (1995), *J. Neurosci.* 15:3970. The agonist potency profile for Group I mGluRs is quisqualate>glutamate=ibotenate>(2S,1'S,2'S)-2-carboxy-cyclopropyl)glycine (L-CCG-I)>(1S,3R)-1-aminocyclopentane-1,3-dicarboxylic acid (ACPD). Quisqualate is relatively selective for Group I receptors, as compared to Group II and Group III mGluRs, but it also potently activates ionotropic AMPA receptors. Pin & Duvoisin (1995), *Neuropharmacology* 34:1; Knopfel et al. (1995), *J. Med. Chem.* 38:1417.

The Group II mGluRs include mGluR2 and mGluR3. Activation of these receptors as expressed in CHO cells inhibits adenlyl cyclase activity via the inhibitory G protein, $G_i$, in a pertussis toxin-sensitive fashion. Tanabe et al. (1992), *Neuron* 8:169; Tanabe et al. (1993), *J. Neurosci.* 13:1372. The agonist potency profile for Group II receptors is L-CCG-I>glutamate>A CPD>ibotenate>quisqualate. Preliminary studies suggest that L-CCG-I and (2S,1'R,2'R,3'R)-2-(2,3-dicarboxycyclopropyl)glycine (DCG-IV) are both relatively selective agonists for the Group II receptors versus other mGluRs (Knopfel et al. (1995), *J. Med. Chem.* 38:1417), but DCG-IV does exhibit agonist activity at iGluRs as well (Ishida et al. (1993), *Br. J. Pharmacol.* 109:1169).

The Group III mGluRs include mGluR4, mGluR6, mGluR7 and mGluR8. Like the Group II receptors, these mGluRs are negatively coupled to adenylyl cyclase to inhibit intracellular cAMP accumulation in a pertussis toxin-sensitive fashion when expressed in CHO cells. Tanabe et al. (1993), *J. Neurosci.* 13:1372; Nakajima et al. (1993), *J. Biol. Chem.* 268:11868; Okamoto et al. (1994), *J. Biol. Chem.* 269: 1231; Duvoisin et al. (1995), *J. Neurosci.* 15:3075. As a group, their agonist potency profile is (S)-2-amino-4-phosphonobutyric acid (L-AP4)>glutamate>ACPD>quisqualate, but mGluR8 may differ slightly with glutamate being more potent than L-AP4. Knopfel et al. (1995), *J. Med. Chem.* 38:1417; Duvoisin et al. (1995), *J. Neurosci.* 15:3075. Both L-AP4 and (S)-serine-O-phosphate (L-SOP) are relatively selective agonists for the Group III receptors.

Finally, the eight mGluR subtypes have unique patterns of expression within the mammalian CNS that in many instances are overlapping. Masu et al. (1991), *Nature* 349: 760; Martin et al. (1992), *Neuron* 9:259; Ohishi et al. (1993), *Neurosci.* 53:1009; Tanabe et al. (1993), *J. Neurosci.* 13:1372; Ohishi et al. (1994), *Neuron* 13:55; Abe et al. (1992), *J. Biol. Chem.* 267:13361; Nakajima et al. (1993), *J. Biol. Chem.* 268:11868; Okamoto et al. (1994), *J. Biol. Chem.* 269:1231; Duvoisin et al. (1995), *J. Neurosci.* 15:3075. As a result, certain neurons may express only one particular mGluR subtype, while other neurons may:express multiple subtypes that maybe localized to similar and/or different locations on the cell (e.g., postsynaptic dendrites and/or cell bodies versus presynaptic axon terminals). Therefore, the functional consequences of mGluR activation on a given neuron will depend on the particular mGluRs being expressed, the receptors' affinities for glutamate and the concentrations of glutamate the cell is exposed to, and signal transduction pathways activated by the receptors, and the locations of the receptors on the cell. A further level of complexity may be introduced by multiple interactions between mGluR-expressing neurons in a given brain region.

As a result of these complexities, and the lack of subtype-specific mGluR agonists and antagonists, the roles of particular mGluRs in physiological and pathophysiological processes affecting neuronal function are not well defined. Still, work with the available agonists and antagonists has yielded some general insights about the Group I mGluRs as compared to the Group II and Group III mGluRs.

Attempts at elucidating the physiological roles of Group I mGluRs suggest that activation of these receptors elicits neuronal excitation. Various studies have demonstrated that ACPD can produce postsynaptic excitation upon application to neurons in the hippocampus, cerebral cortex, cerebellum, and thalamus as well as other brain regions. Evidence indicates that this excitation is due to direct activation of postsynaptic mGluRs, but it has also been suggested to be mediated by activation of presynaptic mGluRs resulting in increased neurotransmitter release. Baskys (1992), *Trends Pharmacol. Sci.* 15:92; Schoepp (1994), *Neurochem. Int.* 24:439; Pin & Duvoisin (1995), *Neuropharmacology* 34:1. Pharmacological experiments implicate Group I mGluRs as the mediators of this excitation. The effect of ACPD can be reproduced by low concentrations of quisqualate in the presence of iGluR antagonists (Hu & Storm (1991), *Brain Res.* 568:339; Greene et al. (1992), *Eur. J. Pharmacol.* 226:279), and two phenylglycine compounds known to activate mGluR1, (S)-3-hydroxyphenylglycine ((S)-3HPG) and (S)-3,5-dihydroxyphenylglycine ((S)-DHPG), also produce the excitation (Watkins & Collingridge (1994), *Trends Pharmacol. Sci.* 15:333). In addition, the excitation can be blocked by (S)-4-carboxyphenylglycine ((S)-4CPG), (S)-4-carboxy-3-hydroxyphenylglycine ((S)-4C3HPG) and (+)-alpha-methyl-4-carboxyphenylglycine ((+)-MCPG), compounds known to be mGluR1 antagonists. Eaton et al. (1993), *Eur. J. Pharmacol.* 244:195; Watkins & Collingridge (1994), *Trends Pharmacol. Sci.* 15:333.

Other studies examining the physiological roles of mGluRs indicate that activation of presynaptic mGluRs can block both excitatory and inhibitory synaptic transmission by inhibiting neurotransmitter release. Pin & Duvoisin (1995), *Neuropharmacology* 34:1. Presynaptic blockade of excitatory synaptic transmission by ACPD has been observed on neurons in the visual cortex, cerebellum, hippocampus, striatum and amygdala (Pin et al. (1993), *Curr. Drugs: Neurodegenerative Disorders* 1:111), while similar blockade of inhibitory synaptic transmission has been demonstrated in the striatum and olfactory bulb (Calabresi et al. (1992), *Neurosci. Lett.* 139:41; Hayashi et al. (1993), *Nature* 366:687). Multiple pieces of evidence suggest that Group II mGluRs mediate this presynaptic inhibition. Group II mGluRs are strongly coupled to inhibition of adenylyl cyclase, like $α_2$-adrenergic and $5HT_{1A}$-serotonergic receptors which are known to mediate presynaptic inhibition of neurotransmitter release in other neurons. The inhibitory effects of ACPD can also be mimicked by L-CCG-I and DCG-IV, which are selective agonists at Group II mGluRs. Hayashi et al. (1993), *Nature* 366:687; Jane et al. (1994), *Br. J. Pharmacol.* 112:809. Moreover, it has been demonstrated that activation of mGluR2 can strongly inhibit presynaptic, N-type calcium channel activity when the receptor is expressed in sympathetic neurons (Ikeda et al. (1995), *Neuron* 14:1029), and blockade of these channels is known to inhibit neurotransmitter release. Finally, it has been observed that L-CCG-I, at concentrations selective for Group II mGluRs, inhibits the depolarization-evoked release of $^3$H-aspartate from rat striatal slices. Lombardi et al. (1993), *Br. J. Pharmacol.* 110:1407. Evidence for physiological effects of Group II mGluR activation at the postsynaptic level is limited. However, one study suggests that postsynaptic actions of L-CCG-I can inhibit NMDA receptor activation in cultured mesencephalic neurons. Ambrosini et al. (1995), *Mol. Pharmacol.* 47:1057.

Physiological studies have demonstrated that L-AP4 can also inhibit excitatory synaptic transmission on a variety of CNS neurons. Included are neurons in the cortex, hippocampus, amygdala, olfactory bulb and spinal cord. Koerner & Johnson (1992), *Excitatory Amino Acid Receptors; Design of Agonists and Antagonists*, p. 308; Pin et al. (1993), *Curr. Drugs: Neurodegenerative Disorders* 1:111. The accumulated evidence indicates that the inhibition is mediated by activation of presynaptic mGluRs. Since the effects of L-AP4 can be mimicked by L-SOP, and these two agonists are selective for Group III mGluRs, members of this mGluR group are implicated as the mediators of the presynaptic inhibition. Schoepp (1994), *Neurochem. Int.* 24:439; Pin & Duvoisin (1995), *Neuropharmacology* 34:1. In olfactory bulb neurons it has been demonstrated that L-AP4 activation of mGluRs inhibits presynaptic calcium currents. Trombley & Westbrook (1992), *J. Neurosci.* 12:2043. It is therefore likely that the mechanism of presynaptic inhibition produced by activation of Group III mGluRs is similar to that for Group II mGluRs, i.e. blockade of voltage-dependent calcium channels and inhibition of neurotransmitter release. L-AP4 is also known to act postsynaptically to hyperpolarize ON bipolar cells in the retina. It has been suggested that this action may be due to activation of a mGluR, which is coupled to the cGMP phosphodiesterase in these cells. Schoepp (1994), *Neurochem. Int.* 24:439; Pin & Duvoisin (1995), *Neuropharmacology* 34:1.

Metabotropic glutamate receptors have been implicated as playing roles in a number of normal processes in the mammalian CNS. Activation of mGluRs has been demonstrated to be a requirement for the induction of hippocampal long-term potentiation and cerebellar long-term depression. Bashir et al. (1993), *Nature* 363:347; Bortolotto et al. (1994), *Nature* 368:740; Aiba et al. (1994), *Cell* 79:365; Aiba et al. (1994), *Cell* 79:377. A role for mGluR activation in nociception and analgesia has also been demonstrated. Meller et al. (1993), *Neuroreport* 4:879. In addition, mGluR activation has been suggested to play a modulatory role in a variety of other normal processes including: synaptic transmission, neuronal development, neuronal death, synaptic plasticity, spatial learning, olfactory memory, central control of cardiac activity, waking, motor control, and control of the vestibulo-ocular reflex (for reviews, see Nakanishi (1994), *Neuron* 13: 1031; Pin & Duvoisin (1995), *Neuropharmacology* 34:1; Knopfel et al. (1995), *J. Med. Chem.* 38:1417).

From the foregoing, it will be appreciated that it would be an advancement in the art to identify and characterize novel human metabotropic glutamate receptors and the nucleic acids that code for such receptors. It would be a further advancement to provide methods for screening for agonists, antagonists, and modulatory molecules that act on such receptors.

Such receptors, nucleic acids, and methods are disclosed and claimed herein.

4. BRIEF SUMMARY OF THE INVENTION

The present invention relates to (1) nucleic acids encoding a newly identified splice variant of human metabotropic glutamate receptor 5 protein and fragments thereof; (2) the metabotropic glutamate receptor protein and fragments thereof; (3) chimeric receptor molecules having one or more domains derived from the new metabotropic glutamate receptor and one or more domains derived from a different receptor; (4) cell lines expressing the metabotropic glutamate receptor protein and fragments thereof; (5) uses of such molecules, nucleic acids, proteins, and cell lines; (6) methods of screening for a compound that binds to or modulates the activity of the metabotropic glutamate receptor; and (7) compounds and methods for modulating the metabotropic glutamate receptor activity and binding to the metabotropic glutamate receptor. Such compounds preferably act as agonists, antagonists, or allosteric modulators of one or more of the metabotropic glutamate receptor activities. By modulating the metabotropic glutamate receptor activities, different effects can be produced, such as anticonvulsant effects, neuroprotectant effects, analgesic effects, psychotropic effects and cognition-enhancement effects.

Metabotropic glutamate receptors have been suggested to play roles in a variety of pathophysiological processes and disease states affecting the CNS. These include stroke, head trauma, anoxic and ischemic injuries, hypoglycemia, epilepsy, anxiety, and neurodegenerative diseases such as Alzheimer's disease. Schoepp & Conn (1993), *Trends Pharmacol. Sci.* 14:13; Cunningham et al. (1994), *Life Sci.* 54:135; Hollman & Heinemann (1994), *Ann. Rev. Neurosci.* 17:31; Pin & Duvoisin (1995), *Neuropharmacology* 34:1; Knopfel et al. (1995), *J. Med. Chem.* 38:1417. Much of the pathology in these conditions is thought to be due to excessive glutamate-induced excitation of CNS neurons. Since Group I mGluRs appear to increase glutamate-mediated neuronal excitation via postsynaptic mechanisms and enhanced presynaptic glutamate release, their activation may contribute to the pathology. Therefore, selective antagonists of these receptors could be therapeutically beneficial, specifically as neuroprotective agents or anticonvulsants. In contrast, since activation of Group II and Group III mGluRs inhibits presynaptic glutamate release and the subsequent excitatory neurotransmission, selective agonists for these receptors might exhibit similar therapeutic utilities. Thus, the various mGluR subtypes may represent novel targets for CNS drug development.

Preliminary studies assessing therapeutic potentials with the available mGluR agonists and antagonists have yielded seemingly contradictory results. For example, it has been reported that application of ACPD onto hippocampal neurons leads to seizures and neuronal damage. Sacaan & Schoepp (1992), *Neurosci. Lett.* 139:77; Lipparti et al. (1993), *Life Sci.* 52:85. But, other studies indicate that. ACPD can inhibit epileptiform activity (Taschenberger et al. (1992), *Neuroreport* 3:629; Sheardown (1992), *Neuroreport*. 3:916), and can also exhibit neuroprotective properties (Koh et al. (1991), *Proc. Natl. Acad. Sci. USA* 88:9431; Chiamulera et al. (1992), *Eur. J. Pharmacol.* 216:335; Siliprandi et al. (1992), *Eur. J. Pharmacol.* 219:173; Pizzi et al. (1993), *J. Neurochem.* 61:683). It is likely that these opposing results are due to ACPD's lack of selectivity and activation of different mGluR subtypes. A reasonable explanation for the results is that Group I mGluRs were activated in the former studies to enhance excitatory neurotransmission, while the latter effects were mediated by activation of Group II and/or Group III mGluRs to inhibit presynaptic glutamate release, and diminish excitatory neurotransmission. The observations that (S)-4C3HPG, a Group I mGluR antagonist and Group II mGluR agonist, protects against audiogenic seizures in DBA/2 mice (Thomsen et al. (1994), *J. Neurochem.* 62:2492); while the Group II mGluR selective agonists DCG-IV and L-CCG-I protect neurons from NMDA- and KA-induced toxicity (Bruno et al. (1994), *Eur. J.*

*Pharmacol.* 256:109; Pizzi et al., *J. Neurochem.* 61:683) are also consistent with this interpretation.

It is evident that the currently available mGluR agonists and antagonists may be of limited use, both as research tools and potential therapeutic agents, as a result of their lack of potency and selectivity. In addition, since these compounds are for the most part amino acids or amino acid derivatives, they have limited bioavailability, which hampers in vivo studies assessing mGluR physiology, pharmacology and therapeutic potential. The identification of agonists and antagonists with a high degree of potency and selectivity for individual mGluR subtypes is therefore the most important requirement to increase the understanding of various mGluRs' roles in physiological and pathophysiological processes in the mammalian CNS. High-throughput screening of chemical libraries using cells stably transfected with individual, cloned mGluRs may offer a promising approach to identify new lead compounds which are active on the individual receptor subtypes. Knopfel et al. (1995), *J. Med. Chem.* 38:1417. These lead compounds could serve as templates for extensive chemical modification studies to further improve potency, mGluR subtype selectivity, and important therapeutic characteristics such as bioavailability.

The preferred use of the receptor and methods of the present invention is to screen for compounds which modulate the activity of the novel metabotropic glutamate receptor. However, other uses are also contemplated, including diagnosis and treatment. Such uses are based on the novel metabotropic glutamate receptor identified herein, the amino acid sequence of which is provided in SEQ ID NO: 2, and the DNA coding sequence is provided in SEQ ID NO: 1 (representing the open reading frame (ORF) of human mGluR5d, nucleotides 1-2826).

Thus, in a first aspect, the invention provides a purified or isolated nucleic acid molecule at least 15 nucleotides in length. This nucleic acid codes for at least five contiguous amino acid residues of a unique portion of a metabotropic glutamate receptor protein which has the amino acid sequence provided in SEQ ID NO: 2, a metabotropic glutamate receptor protein which is a contiguous portion of SEQ ID NO: 2, or a functional equivalent of such amino acid sequences. Preferably, the metabotropic glutamate receptor protein is a human protein. In particular embodiments, the nucleic acid molecule comprises a genomic DNA sequence, a cDNA sequence, or an RNA sequence. In preferred embodiments, the glutamate receptor protein comprises SEQ ID NO: 2 or a functional equivalent of that sequence. In certain other embodiments, the glutamate receptor protein comprises residues 861 to 942 of the amino acid sequence of SEQ ID NO: 2; these residues form the unique cytoplasmic tail of mGluR5d. Of particular interest are nucleic acid molecules encoding essentially a full size novel metabotropic glutamate receptor protein. Therefore, in preferred embodiments, the nucleic acid molecule encodes the amino acid sequence of SEQ ID NO: 2, or of amino acid residues of 861 to 942 of SEQ ID NO: 2, or of a functional equivalent of those sequences.

It is recognized that a large, yet finite number of different nucleic acid sequences will code for the same amino acid sequence due to the redundancy of the genetic code. Such alternative coding sequences are within the scope of the above aspect of the invention.

In a preferred embodiment, the nucleic acid molecule encoding the amino acid sequence of SEQ ID NO: 2 has the nucleic acid sequence of SEQ ID NO: 1. Also in preferred embodiments, the nucleic acid molecule comprises at least 15 or 50 contiguous nucleotides of the nucleic acid sequence SEQ ID NO: 1 or of a sequence substantially complementary thereto.

Since the use of a modified metabotropic glutamate receptor protein is advantageous in certain applications, in a preferred embodiment, the invention also provides an isolated or purified nucleic acid molecule encoding an amino acid sequence which comprises an extracellular domain which is part of the amino acid sequence of SEQ ID NO: 2. In this embodiment, the encoded amino acid sequence is substantially free of membrane spanning domain and intracellular domain portions contained in the amino acid sequence of SEQ ID NO: 2. Likewise, in other particular embodiments, the invention provides other isolated or purified nucleic acid molecules encoding one or more domains which are part of the amino acid sequence of SEQ ID NO: 2, but which do not include at least one such domain. Thus, the invention provides nucleic acid molecules which encode an intracellular domain that is free of transmembrane and extracellular domains, or a transmembrane domain that is free of intracellular and extracellular domains, or an extracellular domain of a metabotropic glutamate receptor that is substantially free of the membrane spanning domains of the metabotropic glutamate receptor, or extracellular and membrane spanning domains, which are substantially free of the intracellular domain. Similarly, in particular embodiments, the nucleic acid encodes a metabotropic glutamate receptor that is substantially free of at least one membrane spanning domain portion or a metabotropic glutamate receptor that is substantially free of the extracellular domain of the metabotropic glutamate receptor, or a contiguous multiple-trans-membrane domain including intervening intracellular and extracellular domains, but substantially free of N-terminal extracellular and C-terminal intracellular domains of SEQ ID NO: 2 (e.g., a seven-transmembrane domain).

In further preferred embodiments, the nucleic acid molecule encodes an extracellular domain of SEQ ID NO: 2, transcriptionally coupled to a second nucleic acid molecule which encodes transmembrane and intracellular domains of a protein which is not a metabotropic glutamate receptor protein (i.e., a non-metabotropic glutamate receptor); the purified nucleic acid encodes a fusion protein composed of an N-terminal extracellular domain contiguous with a seven-transmembrane domain of SEQ ID NO: 2 and is transcriptionally coupled to nucleic acid encoding a C-terminal intracellular domain of a non-metabotropic glutamate receptor; the purified nucleic acid encodes a fusion protein composed of an N-terminal extracellular domain contiguous with a seven-transmembrane domain of SEQ ID NO: 2 and is transcriptionally coupled to nucleic acids encoding multiple intracellular domains of a non-metabotropic glutamate receptor.

Since it is advantageous in certain applications to utilize the complementary or anticoding DNA strand, the invention also provides an isolated or purified nucleic acid molecule which has a sequence substantially complementary to the sequence of a nucleic acid molecule of the above aspect.

In the context of this invention, the term purified, means that the specified nucleic acid molecule or polypeptide has been separated from other nucleic acid molecules or polypeptides, respectively, with which it is found in such a manner that it forms a substantial fraction of the total nucleic acids or polypeptides present in a preparation. Preferably, the specified molecule constitutes at least 1, 5, 10, 50, 75, 85, or 95 percent or more of the molecules of that type (nucleic acid or polypeptide) present in a preparation.

By "isolated" in reference to nucleic acid, polypeptides, or other biomolecules of this invention is meant the molecule is present in a form (i.e., its association with other molecules) other than found in nature. For example, an isolated receptor nucleic acid is separated from one or more nucleic acids which are present on the same chromosome, and an isolated polypeptide is separated from a substantial fraction of the other polypeptides with which it is normally found in nature. Preferably, the isolated nucleic acid or polypeptide is separated from at least 90% of the other nucleic acids present on the same chromosome or polypeptides normally found in the same cell. An example of isolated nucleic acid is recombinant nucleic acid. In this application, the term isolated nucleic acid is distinct from clones existent in a library of clones. It refers to a particular clone having the designated material encoded therein, isolated from other such clones. It can be created by standard recombinant methods to exist within a test-tube or within a desired cell or organism. It is preferably the only nucleic acid cloned within a standard vector, and may or may not contain the naturally occurring control sequences associated with it. Thus, it contains nucleic acid isolated from its natural environment and known to have the sequence claimed to be present. It is preferably a homogenous preparation of nucleic acid separate from other cellular components and from other nucleic acids.

In referring to the nucleic acids and polypeptides of the present invention, the term "unique" refers to a difference in sequence between a nucleic acid molecule of the present invention and the corresponding sequence of other receptor proteins, including other metabotropic glutamate receptor proteins. Thus, the sequences differ by at least one, but preferably a plurality of nucleotides or amino acid residues.

By "substantially complementary" is meant that the purified nucleic acid can hybridize to the complementary sequence region in a specific nucleic acid under stringent hybridization conditions. Such nucleic acid sequences are particularly useful as hybridization detection probes to detect the presence of nucleic acid encoding a particular receptor. Under stringent hybridization conditions, only highly complementary nucleic acid sequences hybridize. Preferably, such conditions prevent hybridization of nucleic acids having 4 or more mismatches out of 20 contiguous nucleotides, more preferably 2 or more mismatches out of 20 contiguous nucleotides, most preferably one or more mismatch out of 20 contiguous nucleotides. Preferably, the nucleic acid is substantially complementary to at least 15, 20, 27, or 45, contiguous nucleotides of the specific sequence (e.g., in SEQ ID NO: 1).

In the context of the novel receptor and fragments, the term "functional equivalent" refers to a polypeptide that has an activity that can be substituted for one or more activities of a particular receptor or receptor fragment. This is explained in greater detail in the Detailed Description below.

In reference to the different domains of a metabotropic glutamate receptor, the term "substantially free" refers to the absence of at least most of the particular domain, preferably such that essentially none of an activity of interest specific to that domain remains. Thus, a short portion(s) of the particular domain sequence may remain, but does not provide a substantial particular activity normally provided by the intact domain.

By "comprising" it is meant including, but not limited to, whatever follows the word "comprising." Thus use of the term indicates that the listed elements are required, but that other elements are optional and may or may not be present.

By "consisting essentially of" is meant that the listed elements are required, but that other elements are optional and may or may not be present depending upon whether or not they affect the activity or action of the listed elements.

Isolated or purified polypeptides corresponding to the nucleic acid molecules of the above aspects are also provided by the present invention. Therefore, in another aspect, the invention features a purified polypeptide having at least 6 contiguous amino acids of an amino acid sequence provided in SEQ ID NO: 2. In preferred embodiments, the purified polypeptide has at least 12, 18, or 54 contiguous amino acids of SEQ ID NO: 2. In further preferred embodiments, the purified polypeptide comprises residues 861 to 942 of the amino acid sequence of SEQ ID NO: 2, which form the unique cytoplasmic tail of mGluR5d. Other preferred receptor fragments include those having only an extracellular portion, a transmembrane portion, an intracellular portion, and/or a multiple transmembrane portion (e.g., seven transmembrane portion). In a particularly preferred embodiment, the polypeptide comprises the amino acid sequence of SEQ ID NO: 2.

Expression of a recombinant nucleic acid encoding a metabotropic glutamate receptor or receptor fragment is a useful method of producing polypeptides such as those described above. Therefore, in another aspect, the invention provides recombinant nucleic acid encoding a metabotropic glutamate receptor or receptor fragment as described in the first aspect above (i.e., coding for a metabotropic glutamate receptor protein having the amino acid sequence SEQ ID NO: 2 or functional equivalents thereof (i.e., these having one or more of the activities associated with that protein but having a few (1-10) amino acid alterations at non-critical areas which do not affect such activities)), cloned in an expression vector. An expression vector contains the necessary elements for expressing a cloned nucleic acid sequence to produce a polypeptide. An "expression vector" contains a promoter region (which directs the initiation of RNA transcription) as well as the DNA sequences which, when transcribed into RNA, will signal protein synthesis initiation. "Expression vector" includes vectors which are capable of expressing DNA sequences contained therein, i.e., the coding sequences are operably linked to other sequences capable of effecting their expression. It is implied, although not always explicitly stated, that these expression vectors must be replicable in the host organisms, either as episomes or as an integral part of the chromosomal DNA. Clearly, a lack of replicability would render them effectively inoperable. A useful, but not a necessary, element of an effective expression vector is a marker-encoding sequence—i.e., a sequence encoding a protein which results in a phenotypic property (e.g., tetracycline resistance) of the cells containing the protein which permits those cells to be readily identified. In sum, "expression vector" is given a functional definition, and any DNA sequence which is capable of effecting expression of a specified contained DNA code is included in this term, as it is applied to the specified sequence. As such vectors are at present frequently in the form of plasmids, the terms "plasmid" and "expression vector" are often used interchangeably. However, the invention is intended to include such other forms of expression vectors, including viral vectors, which serve equivalent functions and which may, from time to time, become known in the art.

In reference to receptor proteins, "biologically functional" and "functional receptor" indicate that the receptor molecule or portion has a normal biological activity characteristic of the normal receptor in its usual cellular environment, which is relevant in the process of interest. Such a process can be, for example, a binding assay, or a complex cellular response.

Preferably, a functional receptor is capable of participating in the normal cellular response reactions. In reference to an expression vector, "biologically functional" means that the expression vector can be transcribed and the transcription product translated in the cell or expression system of interest.

The terms "transformed" and "transfected" refer to the insertion of a foreign genetic material into a prokaryotic or eukaryotic cell. Such insertion is commonly performed using vectors, such as plasmid or viral vectors, but can also include other techniques known to those skilled in the art.

Recombinant nucleic acid may contain nucleic acid encoding a metabotropic glutamate receptor, receptor fragment, or metabotropic glutamate receptor derivative, under the control of its genomic regulatory elements or under the control of exogenous regulatory elements, including an exogenous promoter. By "exogenous" is meant a promoter that is not normally coupled in vivo transcriptionally to the coding sequence for the metabotropic glutamate receptor.

The expression vector may be used in another aspect of the invention to transform or transfect a prokaryotic or a eukaryotic host cell. Thus, another aspect of the present invention features a recombinant cell or tissue. The recombinant cell or tissue is made up of a recombinant nucleic acid sequence of the first aspect above, and a cell able to express the nucleic acid. Recombinant cells have various uses, including as biological factories to produce polypeptides encoded for by the recombinant nucleic acid, and for producing cells containing a functioning metabotropic glutamate receptor. Cells containing a functioning metabotropic glutamate receptor can be used, for example, to screen for mGluR agonists, antagonists, or allosteric modulators. In preferred embodiments, the cell containing the recombinant nucleic acid encoding a functioning metabotropic glutamate receptor is selected from the group consisting of: central nervous system cell, peripheral nervous system cell, pituitary cell, and hypothalamic cell; and the recombinant nucleic acid encodes at least 12, 18 or 54 contiguous amino acids of SEQ ID NO: 2. In a particular embodiment of the invention, the host cell is an oocyte, for example a *Xenopus* oocyte. In other preferred embodiments, the cell is one of NIH-3T3, HeLa, NG115, CHO, HEK 293 and COS7.

Another aspect of the invention describes a process for the production of a polypeptide product involving growing prokaryotic or eukaryotic host cells transformed or transfected with an expression vector having a nucleic acid molecule which codes for a metabotropic glutamate receptor protein having the amino acid sequence SEQ ID NO: 2, or a portion of that sequence, or a functional equivalent, under suitable nutrient conditions. The host cells are grown in a manner allowing expression of the polypeptide product. In a preferred aspect of the invention, the process further involves isolation of the polypeptide product. "Suitable nutrient conditions" are those which will allow a cell to carry on normal metabolic functions and/or grow. The conditions suitable for a particular cell line or strain will generally differ, but appropriate conditions for each such cell type are known to or can be determined by methods known to those skilled in the art.

Another aspect of the invention features a method of screening for a compound that binds to or modulates the activity of a metabotropic glutamate receptor having the sequence SEQ ID NO: 2. The method involves introducing the metabotropic glutamate receptor and a test compound into an acceptable medium and monitoring the binding or modulation by physically detectable means, thereby identifying the compounds which interact with or modulate the activity of the metabotropic glutamate receptor. Such a compound is useful as a therapeutic molecule to modulate metabotropic glutamate receptor activity or as a diagnostic agent to diagnose patients suffering from a disease characterized by an abnormal metabotropic glutamate activity. In a preferred embodiment, the mGluR is a chimeric receptor having an extracellular domain contained in the amino acid sequence of SEQ ID NO: 2 and an intracellular domain of a different receptor. Such a chimeric receptor allows activation of a cellular pathway not normally activated by the novel mGluR described herein. Also, in a preferred embodiment, the metabotropic glutamate receptor is expressed by a cell and the compound is screened by monitoring the effect of the compound on the cell. More preferably, the cell is a eukaryotic cell. For example, the method can involve contacting a cell containing a recombinant nucleic acid encoding a metabotropic glutamate receptor with the agent and detecting a change in metabotropic glutamate receptor activity. In another preferred embodiment, the method involves a competition binding assay with a labeled known binding agent. Preferably, the method is used to identify a metabotropic glutamate receptor-modulating agent.

The term "physically detectable means" refers herein to the means for detecting the interaction between a modulator or binding compound and the novel metabotropic glutamate receptor molecule. Such means can include, for example, spectroscopic methods (e.g., fluorimetric measurement of $Ca^{2+}$), electrophysiological assays, and biochemical assays (e.g., specific enzyme activity). In addition to a variety of other assays, such biochemical assay can include detection of the activation by a chimeric receptor of a cellular pathway not normally activated by the novel mGluR. Each technique detects a physical property or parameter.

A "chimeric receptor" is one which has an amino acid sequence which is a fusion or association of sequences from two or more different proteins, at least one of which is a receptor protein. Typically in this invention, a chimeric receptor has amino acid sequences constituting domains (such as extracellular, membrane spanning, and intracellular) from two or more different receptor proteins, one of which is the novel mGluR5d of this invention.

Identification of metabotropic glutamate receptor-modulating agents is facilitated by using a high-throughput screening system. High-throughput screening allows a large number of molecules to be tested. For example, a large number of molecules can be tested individually using rapid automated techniques or in combination with using a combinatorial library of molecules. Individual compounds able to modulate metabotropic glutamate receptor activity present in a combinatorial library can be obtained by purifying and retesting fractions of the combinatorial library. Thus, thousands to millions of molecules can be screened in a short period of time. Active molecules can be used as models to design additional molecules having equivalent or increased activity. Such molecules will generally have a molecular weight of 10,000, preferably less than 1,000.

A further aspect of the present invention describes a method of modulating the activity of a metabotropic glutamate receptor having the amino acid sequence of SEQ ID NO: 2, or a portion, or a functional equivalent, and includes the step of contacting the receptor with a compound that modulates one or more activities of the metabotropic glutamate receptor, in general either activating or inhibiting activation of the receptor.

The metabotropic glutamate receptor is contacted with a sufficient amount of a compound to modulate a metabotropic glutamate receptor activity. Modulating metabotropic glutamate receptor activity causes an increase or decrease in a cellular response which occurs upon metabotropic glutamate receptor activation, as described in the Detailed Description below. Typically, the compound either mimics one or more effects of glutamate at the metabotropic glutamate receptor, or blocks one or more effects of glutamate at the metabotropic glutamate receptor (or potentially both). The method can be carried out in vitro or in vivo.

The term "mimics" means that the compound causes a similar effect to be exhibited as is exhibited in response to contacting the receptor with glutamate. "Blocks" means that the presence of the compound prevents one or more of the normal effects of contacting the receptor with glutamate.

In the context of this invention, "in vitro" means that a process is not carried out within or by a living cell(s). However, the process may use cell membranes and other cell parts, or even complete but non-living cells. "In vivo" means that the process is carried out within or by a living cell(s), and thus includes processes carried out within or by complex organisms such as mammals.

With respect to a metabotropic glutamate receptor, "functioning" or "functional" indicates that the receptor has at least some of the relevant biological activities which such a receptor has under normal biological conditions (normal receptor under normal cellular conditions), and preferably substantially all of such activities. These can include, for example, specific binding characteristics and specific enzymatic activity (among others).

Related aspects of the present invention describe agents (e.g., compounds and pharmaceutical compositions) able to bind to the metabotropic glutamate receptor having the amino acid sequence SEQ ID NO: 2, or a portion or functional equivalent thereof. Preferably, the agent can modulate metabotropic glutamate receptor activity.

Other features and advantages of the invention will be apparent from the following description of the preferred embodiments thereof, and from the claims.

5. BRIEF DESCRIPTION OF THE DRAWINGS

A more particular description of the invention briefly described above will be rendered by reference to the appended drawings and graphs. These drawings and graphs only provide information concerning typical embodiments of the invention and, therefore, are not to be considered limiting of its scope.

FIG. 1A shows the amino acid sequence of the 3' end of human mGluR5d (amino acids 803 to 942 of SEQ ID NO: 2).

FIG. 1B shows the amino acid sequence of human mGluR5b (amino acids 896 to 1165 of SEQ ID NO: 7) that is deleted from human mGluR5d. The two starred serine residues correspond to serines at positions 881 and 890 of rat mGluR5a. Gereau & Heineman (1998), Neuron 20:143.

6. DETAILED DESCRIPTION OF THE INVENTION

Figure 2:
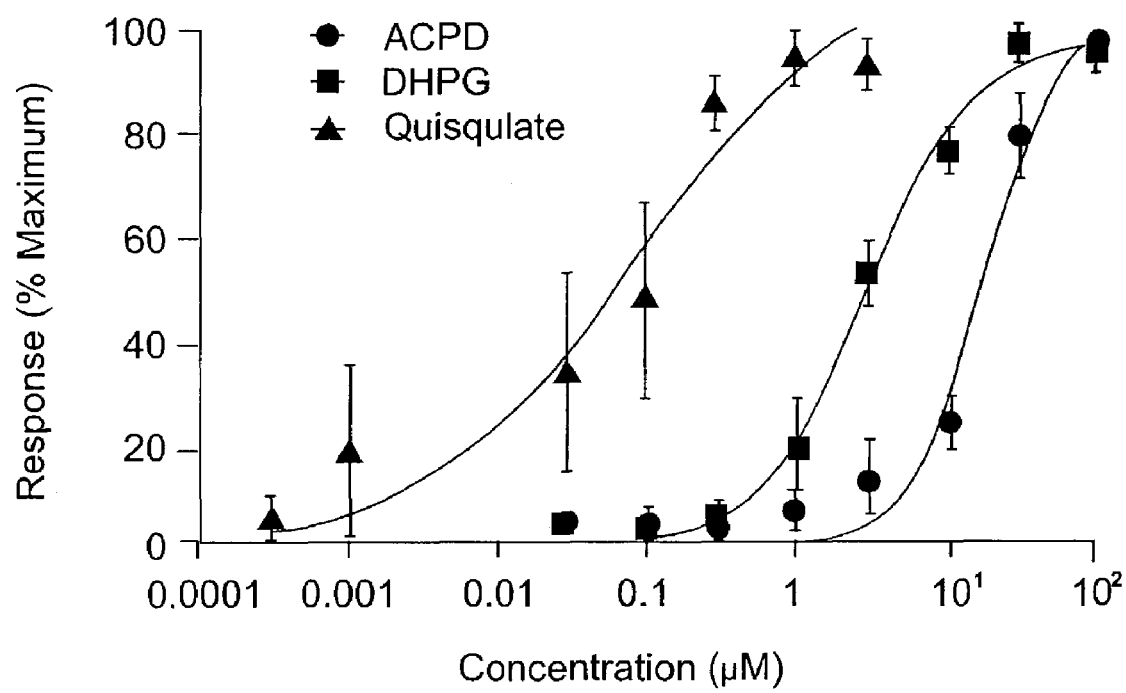
FIG. 2 is a graph depicting the agonist pharmacology of human mGluR5d expressed in HEK293 cells.

The cloning of eight metabotropic glutamate receptor subtypes from rat or mouse has been reported in the scientific literature. These include: rat mGluR1 (Masu et al. (1991), Nature 349:760; Houamed et al. (1991), Science 252:1318; Pin et al. (1992), Proc. Natl. Acad. Sci. USA 89:10331), rat mGluR2 (Tanabe et al. (1992), Neuron 8:169), rat mGluR3 (Tanabe et al. (1992), Neuron 8:169), rat mGluR4 (Tanabe et al. (1992), Neuron 8:169), rat mGluR5 (Abe et al.(1992), J. Biol. Chem. 267:13361), rat mGluR6 (Nakajima et al. (1993), J. Biol. Chem. 268:11868), rat mGluR7 (Okamoto et al. (1994), J. Biol. Chem. 269:1231; Saugstad et al. (1994), Mol. Pharmacol. 45:367) and mouse mGluR8 (Duvoisin et al. (1995), J. Neuroscience 15:3075). The cloning of the human metabotropic glutamate receptor subtypes mGluR1 (Lin et al. (1994), Soc. Neurosci. Abstr. 20:468), mGluR2 (Flor et al. (in press), Eur. J. Neurosci.; Knopfel et al. (1995), J. Med. Chem. 38:1417), mGluR4 (Flor et al. (1994), Neuropharmacol. 34:149), mGluR5 (Minakami et al. (1994), Biochem. Biophys. Res. Commun. 199:1136) and mGluR7 (Flor et al. (1994), Soc. Neurosci. Abstr. 20:468) have also been reported.

U.S. Pat. No. 5,385,831 provides G-protein-coupled glutamate receptors isolated and cloned from rats. U.S. Pat. No. 5,521,297 provides a human metabotropic glutamate receptor and related DNA compounds described by the applicants as a human mGluR1. The subject of the present invention is a novel human metabotropic glutamate receptor. The novel receptor of the present invention is a human metabotropic glutamate receptor that is related to the Group I metabotropic glutamate receptors, which include mGluR1 and mGluR5.

The Applicants are the first to demonstrate the novel human metabotropic glutamate receptor of the present invention, as well as the first to determine the nucleic acid sequence.

6.1 Techniques 6.1.1 Novel mGluR Nucleic Acid Sequence

The invention features nucleic acid sequences encoding metabotropic glutamate receptors and receptor fragments. The nucleic acid sequences may be engineered so as to allow for expression of the receptor sequences in prokaryotic or eukaryotic cells. For example, the entire coding sequence or a fragment thereof, may be combined with one or more of the following in an appropriate expression vector to allow for such expression: (1) an exogenous promoter sequence, (2) a ribosome binding site, (3) a polyadenylation signal, and (4) a secretion signal. Modification can be made in the 5'-untranslated sequences to improve expression in a prokaryotic or eukaryotic cell, or codons may be modified such that while they encode an identical amino acid, that codon may be a preferred codon in the chosen expression system. The use of such preferred codons is described in, for example, Grantham et al. (1981), Nuc. Acids Res., 9:43-74, and Lathe (1985), J. Mol. Biol., 183:1-12. In a preferred embodiment of the current invention, the nucleic acid sequence is that of SEQ ID NO: 1, encoding a novel human metabotropic glutamate receptor.

In addition, a nucleic acid sequence encoding a particular receptor provides for additional tools to obtain other related receptors, for example by providing for nucleic acid hybridization assay probes. Furthermore, the nucleic acid sequences encoding two or more different but related receptors can be analyzed to determine localized regions of sequence conservation. These conserved nucleic acid regions are useful as hybridization probes, or alternatively provide for the design and synthesis of hybridization probes, which can be used to obtain cloned nucleic acids encoding other members of a receptor superfamily. Conserved sequences may be deduced from an analysis of the entire nucleic acid sequence of SEQ ID NO: 1 and comparison of that sequence with the nucleotide sequences encoding other mGluRs.

"Conserved nucleic acid regions" refers to regions within two or more nucleic acids encoding metabotropic glutamate receptors, to which a particular complementary nucleic acid can hybridize under lower stringency conditions. Examples of lower stringency conditions suitable for screening for nucleic acids encoding metabotropic glutamate receptors are provided in the examples below and in Abe et al. (1992), *J. Biol. Chem.* 19:13361. Preferably, conserved nucleic acid regions differ by no more than 7 out of 20 nucleotides.

Uses of nucleic acids encoding cloned receptors or receptor fragments include one or more of the following: (1) producing receptor proteins which can be used, for example, for structure determination, to assay a molecule's activity on a receptor; (2) being sequenced to determine a receptor's nucleotide sequence which can be used, for example, as a basis for comparison with other receptors to determine conserved regions, determine unique nucleotide sequences for normal and altered receptors, and to determine nucleotide sequences to be used as target sites for hybridization detection probes or polymerase chain reaction (PCR) amplification primers; (3) as hybridization detection probes to detect the presence of a native receptor and/or a related receptor in a sample; and (4) as PCR primers to generate particular nucleic acid sequence regions, for example to generate regions to be probed by hybridization detection probes.

In general, the nucleic acid molecules of this invention have nucleic acid sequences encoding full length metabotropic glutamate receptors, metabotropic glutamate receptor fragments, derivatives of full length metabotropic glutamate receptors, and derivatives of metabotropic glutamate receptor fragments useful in the present invention. These include nucleic acid sequences comprising the sequence provided in SEQ ID NO: 1 or nucleic acid sequences which encode the protein sequence provided in SEQ ID NO: 2, or their complementary strands; nucleic acid sequences which hybridize under stringent conditions to the nucleic acid sequence SEQ ID NO: 1 or to fragments thereof; and nucleic acid sequences which, but for the degeneracy of the genetic code would hybridize to the nucleic acid sequence SEQ ID NO: 1.

Preferably, the nucleic acid contains at least 15, 18, 27, and most preferably at least 45, contiguous nucleic acids of a sequence provided in SEQ ID NO: 1. Advantages of longer-length nucleic acid include producing longer-length protein fragments having the sequence of a metabotropic glutamate receptor which can be used, for example, to produce antibodies; increased nucleic acid probe specificity under higher stringency hybridization assay conditions; and more specificity for related metabotropic glutamate receptor nucleic acid under lower stringency hybridization assay conditions.

The present invention also features an isolated and purified nucleic acid which codes for residues 861 to 942 of the amino acid sequence of SEQ ID NO: 2.

Similarly the present invention features nucleic acid encoding a metabotropic glutamate receptor or fragment thereof comprising a nucleic acid sequence encoding at least five contiguous amino acids provided in SEQ ID NO: 2. Preferably, the nucleic acid encodes at least 12, 18, 30, or 54 contiguous amino acids of SEQ ID NO: 2. In certain embodiments, the nucleic acid encodes at least one contiguous, more preferably at least three, six, nine, 12, or 15 contiguous amino acids provided in residues 861 to 942 of SEQ ID NO: 2.

Further, the nucleic acid may be complementary to the nucleic acid sequence coding for either the extracellular binding domain, the transmembrane domain or the intracellular domain portions. The nucleic acid coding for such domains may be transcriptionally coupled to a second nucleic acid sequence from a non-metabotropic glutamate receptor protein. For example, nucleic acid sequence derived from the novel receptor disclosed herein coding for the extracellular domain can be transcriptionally coupled to a second nucleic acid encoding the transmembrane and intracellular coding domain of a non-metabotropic glutamate receptor, or an extracellular binding domain can be transcriptionally coupled to a second nucleic acid encoding the transmembrane and intracellular coding domain of a metabotropic glutamate receptor that is a member of a different class or subclass of mGluR than the receptor having the sequence SEQ ID NO: 2. Such nucleic acids coding for receptor fragments and chimeric receptors are described in, for example, U.S. Pat. No. 5,981,195. Due to the degeneracy of the genetic code, different combinations of nucleotides can code for the same polypeptide. Thus, numerous metabotropic glutamate receptors and receptor fragments having the same amino acid sequences can be encoded for by different nucleic acid sequences.

6.1.1.1 Cloning Using Hybridization Probes and Primers

The presently preferred method for isolating mGluR nucleic acid is based upon hybridization screening. Region-specific primers or probes derived from nucleic acid encoding a metabotropic glutamate receptor such as the nucleic acid sequence SEQ ID NO: 1, or a nucleic acid encoding the amino acid sequence SEQ ID NO: 2, can be used to prime DNA synthesis and PCR amplification, as well as to identify bacterial colonies or phage plaques containing cloned DNA encoding a member of the mGluR family using known methods. See, e.g., Innis et al. (1990), *PCR Protocols* (Academic Press, San Diego, Calif.); Sambrook et al. (1989), *Molecular Cloning* (Cold Spring Harbor Laboratory Press).

6.1.1.1.1 PCR Cloning

Primer hybridization specificity to target nucleic acid encoding a mGluR can be adjusted by varying the hybridization conditions. When carrying out hybridization at higher stringency conditions of 50-60° C., sequences which are greater than about 76% homologous to the primer will be amplified. When employing lower stringency conditions, by carrying out hybridization at 35-37° C., sequences which are greater than about 40-50% homologous to the primer will be amplified.

Analysis of metabotropic glutamate receptors indicates that they are G-protein-coupled receptors having seven conserved, putative transmembrane domains. One particularly useful approach is to employ degenerate primers homologous to the conserved, putative transmembrane domains and to amplify DNA regions encoding these sequences using polymerase chain reaction (PCR). Thus, such oligonucleotide primers are mixed with genomic DNA or cDNA prepared from RNA isolated from the tissue of choice and PCR carried out. Some experimentation maybe required to specifically amplify novel G-protein-coupled receptor sequences from the tissue of choice since these are not necessarily identical to already known G-protein-coupled receptors, but this is well understood by those of ordinary skill in the art. See, e.g., Buck & Axel (1991), *Cell* 65:175-187.

6.1.1.1.2 Hybridization Assay Probes

Hybridization assay probes can be designed based on sequence information obtained from cloned mGluRs and amino acid sequences encoding such receptors such as the novel mGluR that is the subject of this invention. Hybridization assay probes can be designed to detect the presence of a particular nucleic acid target sequence perfectly complementary to the probe and target sequences of lesser complementarity by varying the hybridization conditions and probe design.

DNA probes targeted to metabotropic glutamate receptors can be designed and used under different hybridization conditions to control the degree of specificity needed for hybridization to a target sequence. Factors affecting probe design, such as length, G and C content, possible self-complementarity, and wash conditions, are known in the art. See, e.g., Sambrook et al. (1989), *Molecular Cloning* (Cold Spring Harbor Laboratory Press). Sambrook et al. also discusses the design and use of degenerate probes based on sequence polypeptide information.

As a general guideline, high stringency conditions (hybridization at 50-65° C., 5×SSPC, 50% formamide, wash at 50-65° C., 0.5×SSPC) can be used to obtain hybridization between nucleic acid sequences having regions which are greater than about 90% complementary. Low stringency conditions (hybridization at 35-37° C., 5×SSPC, 40-45% formamide, wash at 42° C. 2×SSPC) be used so that sequences having regions which are greater than 35-45% complementary will hybridize to the probe.

Many tissues or cells can be used as a source for genomic DNA, including for example placenta or peripheral blood leukocytes. However, with respect to RNA, the most preferred source is a tissue or cell type which expresses elevated levels of the desired metabotropic glutamate receptor family member.

6.1.2 Novel Metabotropic Glutamate Receptor Nucleic Acid Derivatives

The isolated nucleic acid sequences of the invention also provide for the creation of modified nucleic acids with practical utility. The nucleic acid sequence can be mutated in vitro or in vivo to, for example, (1) create variations in coding regions, thereby generating metabotropic glutamate receptor variants or derivatives; (2) form new restriction endonuclease sites or destroy preexisting ones, to facilitate further in vitro modification or (3) form new splice sites to create mGluR splice variants. Standard recombinant techniques for mutagenesis such as in vitro site-directed mutagenesis (Hutchinson et al. (1978), *J. Biol. Chem.* 253: 6551; Sambrook et al., Chapter 15), use of TAB® linkers (Pharmacia), and PCR-directed mutagenesis can be used to create such mutations.

Additionally, nucleic acid sequences of the current invention can be engineered and recombined with nucleic acids encoding other receptors to form nucleic acids encoding chimeric receptors. Such nucleic acids encoding chimeric receptors are described in, for example, pending U.S. Pat. No. 5,981,195.

Preferred receptor fragments include those having functional receptor activity, a binding site, epitope for antibody recognition (typically at least six amino acids), and/or a site which binds a metabotropic glutamate receptor agonist or antagonist. Other preferred receptor fragments include those having only an extracellular portion, a transmembrane portion, an intracellular portion, and/or a multiple transmembrane portion (e.g., seven transmembrane portion). Such receptor fragments have various uses such as being used to obtain antibodies to a particular region and being used to form chimeric receptors with fragments of other receptors to create a new receptor having unique properties. Such purified receptor fragments and chimeric receptors are described in, for example, U.S. Pat. No. 5,981,195. Thus, as described in the Summary above, the invention features derivatives of full-length metabotropic glutamate receptors and fragments thereof having the same, or substantially the same, activity as the full-length parent metabotropic glutamate receptor or fragment. Such derivatives include amino acid addition(s), substitution(s), and deletion(s) to the receptor which do not prevent the derivative receptor from carrying out one or more of the activities of the parent receptor. Functional equivalents of a metabotropic glutamate receptor protein include, but are not limited to, such derivatives.

6.1.3 Transfected Cell Lines

Nucleic acid expressing a functional metabotropic glutamate receptor can be used to create transfected cell lines which functionally express a specific metabotropic glutamate receptor. Such cell lines have a variety of uses such as being used for high-throughput screening for molecules able to modulate metabotropic glutamate receptor activity; and being used to assay binding to a metabotropic glutamate receptor, and for production of metabotropic glutamate receptor peptides.

A variety of cell lines are capable of coupling exogenously expressed receptors to endogenous functional responses. A number of these cell lines (e.g., NIH-3T3, HeLa, NG115, CHO, HEK 293 and COS7) can be tested to confirm that they lack an endogenous metabotropic glutamate receptor. Those lines lacking a response to external glutamate can be used to establish stably transfected cell lines expressing the cloned metabotropic glutamate receptor.

Production of these stable transfectants is accomplished by transfection of an appropriate cell line with a eukaryotic expression vector, such as pCEP4, in which the coding sequence for the metabotropic glutamate receptor cDNA has been cloned into the multiple cloning site. These expression vectors contain a promoter region, such as the human cytomegalovirus promoter (CMV), that drive high-level transcription of cDNAs in a variety of mammalian cells. In addition, these vectors contain genes for the selection of cells that stably express the cDNA of interest. The selectable marker in the pCEP4 vector encodes an enzyme that confers resistance to hygromycin, a metabolic inhibitor that is added to the culture to kill the nontransfected cells. A variety of expression vectors and selection schemes are usually assessed to determine the optimal conditions for the production of metabotropic glutamate receptor-expressing cell lines for use in high-throughput screening assays.

The most effective method for transfection of eukaryotic cell lines with plasmid DNA varies with the given cell type. The metabotropic glutamate receptor expression construct will be introduced into cultured cells by the appropriate technique, either calcium phosphate precipitation, DEAE-dextran transfection, lipofection or electroporation.

Cells that have stably incorporated the transfected DNA will be identified by their resistance to selection media, as described above, and clonal cell lines will be produced by expansion of resistant colonies. The expression of the metabotropic glutamate receptor cDNA by these cell lines will be assessed by solution hybridization and Northern blot analysis. Functional expression of the receptor protein will be determined by measuring the inhibition of adenylate cyclase activity and the subsequent reduction in cAMP accumulation in response to externally applied metabotropic glutamate receptor agonists; or by measuring the mobilization of intracellular calcium in response to externally applied metabotropic glutamate receptor agonists.

In a preferred embodiment of the current invention, the nucleic acid used to create a stably transfected eukaryotic cell line codes for SEQ ID NO: 2, more preferably, the nucleic acid is that represented by SEQ ID NO: 1, and/or various modified derivatives thereof including: (1) derivatives encoding receptor mutants, (2) derivatives encoding chimeric receptors, or (3) derivatives encoding receptor fragments.

6.1.4 Novel Metabotropic Glutamate Receptor Protein, Derivatives and Fragments

6.1.4.1 Metabotropic Glutamate Receptor Proteins

Recombinant metabotropic glutamate receptor proteins can be expressed in a variety of tissue and cell types including human tissue and cell types. These recombinant metabotropic glutamate receptor proteins can be utilized for a variety of purposes by those skilled in the art. The recombinant receptor proteins can be used as a source of antigen for the production of antibodies directed against metabotropic glutamate receptors, including polyclonal and monoclonal antibodies. In addition, recombinant metabotropic glutamate receptor proteins can be utilized for drug discovery purposes utilizing methods known to those skilled in the art. The recombinant receptor proteins can be utilized to screen (including high through-put screening) for molecules that bind to metabotropic glutamate receptors; as well as to screen for molecules that can modulate metabotropic glutamate receptor activity by acting as agonists, antagonists, or allosteric modulators. Finally, recombinant metabotropic glutamate receptor proteins can be used for structural studies of small molecule drug interactions with metabotropic glutamate receptors; antibody interactions with metabotropic glutamate receptors; or the interactions of other peptides and proteins with metabotropic glutamate receptors. These uses of metabotropic glutamate receptor proteins are not meant to be limiting.

In a preferred embodiment of the current invention, the recombinant metabotropic receptor protein is a human metabotropic glutamate receptor protein, and more specifically it is a recombinant metabotropic glutamate receptor protein having the amino acid sequence represented in SEQ ID NO: 2 or a biologically active portion of that sequence, or a functional equivalent.

6.1.4.2 Metabotropic Glutamate Receptor Derivatives

Derivatives of a particular receptor are functional equivalents to that receptor, having similar amino acid sequence and retaining, to some extent, one or more activities of the related receptor. By "functional equivalent" is meant a protein that has an activity that can be substituted for one or more activities of a particular receptor or receptor fragment. Preferred functional equivalents retain all of the activities of a particular receptor or receptor fragment, however, the functional equivalent may have an activity that, when measured quantitatively, is stronger or weaker than the related receptor, as measured in standard receptor assays, for example, such as those disclosed herein. Preferred functional equivalents have activities that are within 1% to 10,000% of the activity of the related receptor, more preferably between 10% to 1000%, and more preferably within 50% to 500%. Functional equivalents may include, for example, derivatives which contain modifications or amino acid alterations in, for example, the region of a receptor which contains ligand binding activity. Such amino acid alterations may either increase or decrease the binding activity of the receptor with a particular binding agent. Functional equivalents may also include, for example, derivatives which contain modifications or amino acid alterations in the intracellular domain portion of the receptor which may, for example, increase or decrease the activity of the receptor by, for example, increasing or decreasing the cellular response to receptor activation. Derivatives have at least 15% sequence similarity, preferably 70%, more preferably 90%, even more preferably 95% sequence similarity to the related receptor. "Sequence similarity" refers to "homology" observed between amino acid sequences in two different polypeptides, irrespective of polypeptide origin.

The ability of the derivative to retain some activity can be measured using techniques described herein. Derivatives include modification occurring during or after translation, for example, by phosphorylation, glycosylation, crosslinking, acylation, proteolytic cleavage, linkage to an antibody molecule, membrane molecule or other ligand. See Ferguson et al. (1988), *Annu. Rev. Biochem.* 57:285-320.

Specific types of derivatives also include amino acid alterations such as deletions, substitutions, additions, and amino acid modifications. A "deletion" refers to the absence of one or more amino acid residue(s) in the related polypeptide. An "addition" refers to the presence of one or more amino acid residue(s) in the related polypeptide. Additions and deletions to a polypeptide may be at the amino terminus, the carboxy terminus, and/or internal. Amino acid "modification" refers to the alteration of a naturally occurring amino acid to produce a non-naturally occurring amino acid. A "substitution" refers to the replacement of one or more amino acid residue(s) by another amino acid residue(s) in the polypeptide. Derivatives can contain different combinations of alterations including more than one alteration and different types of alterations.

While the effect of an amino acid change varies depending upon factors such as phosphorylation, glycosylation, intrachain linkages, tertiary structure, and the role of the amino acid in the active site or a possible allosteric site, it is generally preferred that the substituted amino acid is from the same group as the amino acid being replaced. To some extent, the following groups contain amino acids which are interchangeable: the basic amino acids lysine, arginine, and histidine; the acidic amino acids aspartic and glutamic acids; the neutral polar amino acids serine, threonine, cysteine, glutamine, asparagine and, to a lesser extent, methionine; the nonpolar aliphatic amino acids glycine, alanine, valine, isoleucine, and leucine (however, because of size, glycine and alanine are more closely related and valine, isoleucine and leucine are more closely related); and the aromatic amino acids phenylalanine, tryptophan, and tyrosine. In addition, although classified in different categories, alanine, glycine, and serine seem to be interchangeable to some extent, and cysteine additionally fits into this group, or may be classified with the polar neutral amino acids.

While proline is a nonpolar neutral amino acid, its replacement represents difficulties because of its effects on conformation. Thus, substitutions by or for proline are not preferred, except when the same or similar conformational results can be obtained. The conformation conferring properties of proline residues may be obtained if one or more of these are substituted by hydroxyproline (Hyp).

Examples of modified amino acids include the following: altered neutral nonpolar amino acids such as amino acids of the formula $H_2N(CH_2)_nCOOH$ where n is 2-6, sarcosine (Sar), t-butylalanine (t-BuAla), t-butylglycine (t-BuGly), N-methyl isoleucine (N-MeIle), and norleucine (Nleu); altered neutral aromatic amino acids such as phenylglycine; altered polar, but neutral amino acids such as citrulline (Cit) and methionine sulfoxide (MSO); altered neutral and nonpolar amino acids such as cyclohexyl alanine (Cha); altered acidic amino acids such as cysteic acid (Cya); and altered basic amino acids such as ornithine (Orn).

Preferred derivatives have one or more amino acid alteration(s) which do not significantly affect the receptor activity of the related receptor protein. In regions of the metabotropic glutamate receptor protein not necessary for receptor activity, amino acids may be deleted, added or substituted with less risk of affecting activity. In regions required for receptor activity, amino acid alterations are less preferred as there is a greater risk of affecting receptor activity. Such alterations should be conservative alterations. For example, one or more amino acid residues within the sequence can be substituted by another amino acid of a similar polarity which acts as a functional equivalent.

Conserved regions tend to be more important for protein activity than non-conserved regions. Standard procedures can be used to determine the conserved and non-conserved regions important for receptor activity using in vitro mutagenesis techniques or deletion analyses and measuring receptor activity as described by the present disclosure.

Derivatives can be produced using standard chemical techniques and recombinant nucleic acid techniques. Modifications to a specific polypeptide may be deliberate, as through site-directed mutagenesis and amino acid substitution during solid-phase synthesis, or may be accidental such as through mutations in hosts which produce the polypeptide. Polypeptides including derivatives can be obtained using standard techniques such as those described above, as well as techniques described by Sambrook et al. (1989), *Molecular Cloning* (Cold Spring Harbor Laboratory Press). For example, Chapter 15 of Sambrook describes procedures for site-directed mutagenesis of cloned DNA.

In a preferred embodiment of the current invention, the polypeptide subject to modification is that of a human metabotropic glutamate receptor, and more specifically, is a polypeptide having the amino acid sequence represented in SEQ ID NO: 2.

6.1.4.3 Metabotropic Glutamate Receptor Fragments

Receptor fragments are portions of metabotropic glutamate receptors. Receptor fragments preferably bind to one or more binding agents which bind to a full-length receptor. Binding agents include ligands, such as glutamate, quisqualate, agonists, antagonists, allosteric modulators, and antibodies which bind to the receptor. Fragments have different uses such as to select other molecules able to bind to a receptor.

Fragments can be generated using standard techniques such as expression of cloned partial sequences of receptor DNA and proteolytic cleavage of a receptor protein. Proteins are specifically cleaved by proteolytic enzymes, such as trypsin, chymotrypsin or pepsin. Each of these enzymes is specific for the type of peptide bond it attacks. Trypsin catalyzes the hydrolysis of peptide bonds whose carbonyl group is from a basic amino acid, usually arginine or lysine. Pepsin and chymotrypsin catalyze the hydrolysis of peptide bonds from aromatic amino acids, particularly tryptophan, tyrosine and phenylalanine.

Alternate sets of cleaved protein fragments are generated by preventing cleavage at a site which is susceptible to a proteolytic enzyme. For example, reaction of the ε-amino group of lysine with ethyltrifluorothioacetate in mildly basic solution yields a blocked amino acid residue whose adjacent peptide bond is no longer susceptible to hydrolysis by trypsin. Goldberger et al. (1962), *Biochemistry* 1:401. Treatment of such a polypeptide with trypsin thus cleaves only at the arginyl residues.

Polypeptides also can be modified to create peptide linkages that are susceptible to proteolytic enzyme-catalyzed hydrolysis. For example, alkylation of cysteine residues with b-haloethylamines yields peptide linkages that are hydrolyzed by trypsin. Lindley (1956), *Nature*, 178:647.

In addition, chemical reagents that cleave polypeptide chains at specific residues can be used. Witcop (1961), *Adv. Protein Chem.* 16:221. For example, cyanogen bromide cleaves polypeptides at methionine residues. Gross & Witkip (1961), *J. Am. Chem. Soc.* 83:1510.

Thus, by treating a metabotropic glutamate receptor, or fragments thereof, with various combinations of modifiers, proteolytic enzymes and/or chemical reagents, numerous discrete overlapping peptides of varying sizes are generated. These peptide fragments can be isolated and purified from such digests by chromatographic methods. Alternatively, fragments can be synthesized using an appropriate solid-state synthetic procedure.

Fragments may be selected to have desirable biological activities. For example, a fragment may include just a ligand binding site. Such fragments are readily identified by those of ordinary skill in the art using routine methods to detect specific binding to the fragment. For example, in the case of a metabotropic glutamate receptor, nucleic acid encoding a receptor fragment can be expressed to produce the polypeptide fragment which is then contacted with a receptor ligand under appropriate association conditions to determine whether the ligand binds to the fragment. Such fragments are useful in screening assays for agonists and antagonists of glutamate.

Other useful fragments include those having only the external portion, membrane-spanning portion, or intracellular portion of the receptor. These portions are readily identified by comparison of the amino acid sequence of the receptor with those of known receptors, or by other standard methodology. These fragments are useful for forming chimeric receptors with fragments of other receptors to create a receptor with an intracellular portion which performs a desired function within that cell, and an extracellular portion which causes that cell to respond to the presence of glutamate, or those agonists or antagonists described herein. For example, chimeric receptors can be constructed such that the intracellular domain is coupled to a desired enzymatic process which can be readily detected by colorimetric, radiometric, luminometric, spectrophotometric or fluorimetric assays and is activated by interaction of the extracellular portion with its native ligand (e.g., glutamate) or agonist and/or antagonists of the invention. Cells expressing such chimeric receptors can be used to facilitate screening of metabotropic glutamate receptor agonists and antagonists.

In a preferred embodiment of the current invention, the polypeptide fragments are fragments of a human metabotropic glutamate receptor, and more specifically, are fragments of the polypeptide having the amino acid sequence represented in SEQ ID NO: 2.

6.1.5 Compounds Targeted to the Novel Metabotropic Glutamate Receptor

The mGluR agonist and antagonist compounds described in the scientific literature are related to the endogenous agonist, glutamate. (For reviews, see Cockcroft et al. (1993); *Neurochem. Int.* 23:583-594; Schoepp & Conn (1993), *Trends Pharmacol. Sci.* 14:13-20; Hollmann & Heinemann (1994), *Annu. Rev. Neurosci.* 17:31-108; Watkins & Collinridge (1994), *Trends Pharmacol. Sci.* 15:333; Knopfel et al. (1995), *J. Med. Chem.* 38:1417.) Such agonist and antagonist compounds have an acidic moiety, usually a carboxylic acid, but sometimes a phosphonic acid. Presumably then, such compounds bind mGluRs at the same site as the amino acid, glutamate. This has been confirmed for methylcarboxyphenylglycine, which was shown to be a competitive antagonist of glutamate. Eaton et al. (1993), *Eur. J. Pharm.—Mol. Pharm. Sect.* 244:195-197. Since these compounds are for the most part amino acids or amino acid derivatives, they have limited bioavailability, which hampers in vivo studies assessing mGluR physiology pharmacology and therapeutic potential. In addition, the currently available mGluR agonists and antagonists are of limited use, both as research tools and potential therapeutic agents, as a result of their lack of potency and selectivity. The identification of agonists and antagonists with a high degree of potency and selectivity for individual mGluR subtypes is therefore the most important requirement to increase the understanding of various mGluRs' roles in physiological and pathophysiological processes in the mammalian CNS.

The isolation of the nucleic acid encoding the novel mGluR of the present invention allows for the receptor's expression in transfected cell lines, and these cells can be utilized to screen for novel compounds capable of binding to and modulating the activity of the novel mGluR. These compounds could bind at the same site as glutamate, or alternatively at novel binding sites on the mGluR protein. Such screening can identify compounds with improved potency and selectivity for the novel mGluR. These compounds may also have other beneficial characteristics such as improved bioavailability. Such compounds would have utility as improved research tools for deducing the novel mGluR's physiological and pathophysiological roles, and as potential therapeutic agents.

Compounds targeted to the novel metabotropic glutamate receptor can have several uses including therapeutic uses and diagnostic uses. Those compounds binding to a metabotropic glutamate receptor and those compounds efficacious in modulating metabotropic receptor glutamate activity can be identified using the procedures described herein. Those compounds which can selectively bind to the metabotropic glutamate receptor can be used therapeutically, or alternatively as diagnostics to determine the presence of the metabotropic glutamate receptor versus other glutamate receptors.

6.1.6 Modulation of Metabotropic Glutamate Receptor Activity

Modulation of metabotropic glutamate receptor activity can be used to produce different effects such as anticonvulsant effects, neuroprotectant effects, analgesic effects, cognition-enhancement effects, and muscle-relaxation effects. Each of these effects has therapeutic applications. Compounds used therapeutically should have minimal side effects at therapeutically effective doses.

Modulating metabotropic glutamate receptor activity causes an increase or decrease in a cellular response which occurs upon metabotropic glutamate receptor activation. Cellular responses to metabotropic glutamate receptor activation vary depending upon the type of metabotropic glutamate receptor activated. Generally, metabotropic glutamate receptor activation causes one or more of the following activities: (1) activation of phospholipase C, (2) increases in phosphoinositide (PI) hydrolysis, (3) intracellular calcium release, (4) activation of phospholipase D, (5) activation or inhibition of adenylyl cyclase, (6) increases or decreases in the formation of cyclic adenosine monophosphate (cAMP), (7) activation of guanylyl cyclase, (8) increases in the formation of cyclic guanosine monophosphate (cGMP), (9) activation of phospholipase $A_2$, (10) increases in arachidonic acid release, and (11) increases or decreases in the activity of ion channels, for example voltage- and ligand-gated ion channels. Inhibition of metabotropic glutamate receptor activation prevents one or more of these activities from occurring.

Activation of a particular metabotropic glutamate receptor refers to the production of one or more activities associated with the type of receptor activated, for example: (1) activation of phospholipase C, (2) increases in phosphoinositide (PI) hydrolysis, (3) intracellular calcium release, (4) activation of adenylyl cyclase, (5) increases in the formation of cyclic adenosine monophosphate (cAMP), (6) activation of phospholipase $A_2$, (7) increases in arachidonic acid release, (8) increases or decreases in ion channel activity.

The ability of a compound to modulate metabotropic glutamate activity can be monitored using electrophysiological and biochemical assays measuring one or more metabotropic glutamate activities. Examples of such assays include the electrophysiological assessment of metabotropic glutamate receptor function in *Xenopus* oocytes expressing cloned metabotropic glutamate receptors, the electrophysiological assessment of metabotropic glutamate receptor function in transfected cell lines (e.g., CHO cells, HEK 293 cells, etc.) expressing cloned metabotropic glutamate receptors, the biochemical assessment of PI hydrolysis and cAMP accumulation in transfected cell lines expressing cloned metabotropic glutamate receptors, the biochemical assessments of PI hydrolysis and cAMP accumulation in rat brain (e.g., hippocampal, cortical, striatal, etc.) slices, fluorimetric measurements of cytosolic $Ca^{2+}$ in cultured rat cerebellar granule cells, and fluorimetric measurements of cytosolic $Ca^{2+}$ in transfected cell lines expressing cloned metabotropic glutamate receptors.

Prior to therapeutic use in a human, the compounds are preferably tested in vivo using animal models. Animal studies to evaluate a compound's effectiveness to treat different diseases or disorders, or exert an effect such as an analgesic effect, a cognition-enhancement effect, or a muscle-relaxation effect, can be carried out using standard techniques.

6.1.7 In Vitro Diagnostics

The different molecules of the present invention can be used to facilitate diagnosis of metabotropic glutamate receptor-related diseases. Diagnosis can be carried out in vitro or in vivo. For example, the molecules of the present invention can be used to assay for defects in metabotropic glutamate receptors.

Nucleic acid probes can be used to identify defects in metabotropic glutamate receptors occurring at the genetic level. For example, hybridization probes complementary to nucleic acid encoding a receptor can be used to clone the receptor. The cloned receptor can be inserted into a cell, such as an oocyte, and its responsiveness to an mGluR ligand determined. Another example of using hybridization assay probes to detect defects involves using the probes to detect mRNA levels or the presence of nucleic acid sequences associated with a particular disease. A decreased mRNA level would be consistent with a decreased amount of expressed receptor.

All publications, patents, and patent applications cited in this application are hereby incorporated by reference in their entirety.

7. EXAMPLES

Examples are provided below to illustrate different aspects and embodiments of the present invention. These examples are not intended in any way to limit the disclosed invention. Rather, they illustrate methodologies by which the novel human mGluR5 splice variant of the present invention may be isolated, expressed in eukaryotic systems, and assessed for functional activity. They also illustrate methodologies by which compounds may be screened to identify those which bind to or modulate the activity of the novel human mGluR5 splice variant.

Example 1

Cloning of a Novel Human mGluR5 Splice Variant

Numbering of nucleotide positions for all the following constructs is such that nucleotide number 1 corresponds to the A of the ATG start codon of the nucleotide sequence encoding the designated protein.

The 5' portion of human mGluR5 was amplified from human hippocampus—Marathon-Ready™ cDNA (CLONTECH Laboratories, Inc.) using PCR primers based on the human mGluR5a cDNA sequence (Genbank Accession No. D28538). The primers used were the Marathon Adaptor Primer (AP1; CLONTECH) and the gene-specific primer, hR5UP (antisense 25-mer, complementary to nucleotides 2301-2325 of human mGluR5). Amplification products were subjected to agarose gel electrophoresis and those corresponding to approximately 2500 bp in size were gel isolated and subcloned into the Bluescript SK(−) plasmid (Stratagene) following digestion of both plasmid and PCR product with NotI and EcoRV restriction endonucleases. DNA sequence analysis of the subclones via double-stranded DNA sequencing with Sequenase Version 2.0 (US Biochemical) confirmed human mGluR5 sequence.

The 3' portion of human mGluR5d was also amplified from human hippocampus—Marathon-Ready™ cDNA (CLONTECH Laboratories, Inc.) using the Marathon Adaptor Primer (AP1; CLONTECH) and the gene-specific primers, hR5DN (sense 25-mer, corresponding to nucleotides 2061-2085 of human mGluR5) and the nested gene-specific primer, R5DN2 (sense, 27-mer, corresponding to nucleotides 2149-2175). Agarose gel electrophoresis revealed multiple products diverse in size. This collection of products was gel isolated and subcloned into the Bluescript SK(−) plasmid (Stratagene) following digestion of both plasmid and PCR products with NotI and EcoRV restriction endonucleases. DNA sequence analysis of the subclones via double-stranded DNA sequencing with Sequenase Version 2.0 (US Biochemical) revealed the presence of a novel 3' splice variant of human mGluR5.

To construct a full-length human mGluR5d ("hmGluR5d") construct, the 5' mGluR5 construct was digested with the restriction endonuclease SacII, blunted with T4 DNA Polymerase, then digested with the NheI. The 3' hmGluR5d construct was digested with PstI, blunted with T4 DNA Polymerase, then digested with NheI. The 5' insert of approximately 2 kb was gel isolated and ligated to the Bluescript SK(−) vector containing the 3' human mGluR5d fragment. The sequence of the resultant full-length human mGluR5d was verified by ABI automated sequence analysis. This construct is referred to as phmGluR5d(SK−).

The full-length human mGluR5d was then subcloned into the mammalian expression vector pcDNA3.1/Hygro(+) vector (Invitrogen) using the restriction endonucleases HindIII and NotI. This construct is referred to as phmGluR5d (Hyg+).

The nucleotide sequence of the human mGluR5d cDNA is depicted in SEQ ID NO: 1. The open reading frame is 2826 bp.

The 2826 bp open reading frame of the human mGluR5d cDNA encodes a 942 amino acid protein (SEQ ID NO: 2). The amino acid sequence of the novel human mGluR5d splice variant is identical to the human mGluR5b amino acid sequence up to residue 895, with a deletion of 270 amino acids within the C-terminal tail (FIGS. 1A & 1B).

Example 2

Construction of a Chimeric Receptor Between the Human Calcium Receptor and the Human mGluR5d Splice Variant This chimera contains the extracellular domain of the human calcium receptor ("CaR") (Garrett et al. (1995), *J. Biol. Chem.* 270:12919) and transmembrane domain and intracellular cytoplasmic tail of the human mGluR5d splice variant. The chimeric junction between the CaR and hmGluR5d was created using a recombinant PCR strategy.

The first reaction used two primers, CA1156 (sense 19-mer, corresponding to nucleotides 1156-1174 of human CaR), and the hybrid primer CA/5 (antisense 42-mer; containing 21 nucleotides complementary to nucleotides 1774-1794 of human CaR and 21 nucleotides complementary to nucleotides 1696-1716 of the human mGluR5d). These primers were used to amplify a 659 bp PCR fragment of human CaR from the plasmid phCaR in Bluescript SK(−).

In a separate PCR reaction using phmGluR5d(SK−) as template, an 800 bp fragment of the human mGluR5d was amplified using a hybrid primer 5/CA (sense 42-mer, exactly complementary to primer CA/5) and oligo 5-2475 m, (antisense 17-mer, complementary to nucleotides 2459-2475 of the human mGluR5d cDNA). The two PCR products generated from the above two reactions were annealed together in equimolar ratios in the presence of the external primers CA1156 and 5-2475 m, and the Pfu DNA polymerase (Stratagene).

The resulting chimeric PCR product was digested with SexA1 (Boehringer Mannheim) and NheI (New England Biolabs) and subcloned into phCaR digested with the same two restriction enzymes. In the final cloning step, the 3' end of human mGluR5d was subcloned into this construct using the restriction enzymes NheI and NotI (both New England Biolabs). The sequence of the resultant chimeric construct, phCaR/hmGluR5d, was verified by ABI automated DNA sequence analysis. The 2925 bp open reading frame (SEQ ID NO: 3) of the hCaR/hmGluR5d chimera encodes a 975 amino acid protein (SEQ ID NO: 4).

The chimeric receptor was then subcloned into the mammalian expression vector pcDNA3.1/Hygro(+) vector (Invitrogen) using the restriction endonucleases HindIII and NotI. This construct is referred to as phCaR/hmGluR5d(Hyg+).

A chimeric receptor having an extracellular domain and seven transmembrane domain of mGluR5d and an intracellular cytoplasmic tail domain of a G-protein-coupled calcium receptor could also be constructed using well-known techniques. See, e.g., U.S. Pat. No. 5,981,195. The amino acid sequence of such a chimeric receptor is given in SEQ ID NO: 6, and a representative nucleotide sequence coding for such a chimeric receptor is given in SEQ ID NO: 5.

Example 3

Functional Activation of the Novel Metabotropic Glutamate Receptor 5 Splice Variant Expressed in *Xenopus* Oocytes This example describes the activation of the novel hmGluR5d splice variant using a *Xenopus* oocyte expression assay. PhmGluR5d(Hyg+) DNA was linearized by restriction enzyme digestion, and capped sense-strand cRNA was synthesized by T7 RNA polymerase transcription (Ambion Message Machine Kit). In vitro-transcribed RNA was concentrated by ethanol precipitation and the size and integrity of the RNA was assessed on a denaturing agarose gel.

Oocytes suitable for injection were obtained from adult female *Xenopus laevis* toads using procedures described in Marcus-Sekura & Hitchcock (1987), *Methods in Enzymology* 152. In vitro-transcribed RNA (~10 ng) encoding the human mGluR5d receptor was injected into *Xenopus* Oocytes. Following injection, oocytes were incubated at 16° C. in MBS containing 1 mM $CaCl_2$ for 2 to 7 days prior to electrophysiological recording. Following the incubation, the oocytes were voltage-clamped using standard electrophysiological techniques. Hille (1992), *Ionic Channels of Excitable Membranes*, pp. 30-33 (Sinauer Associates, Inc., Sunderland, Mass.). Activation of the hmGluR5d receptor was detected by increases in the calcium-activated chloride current.

Figure 3:
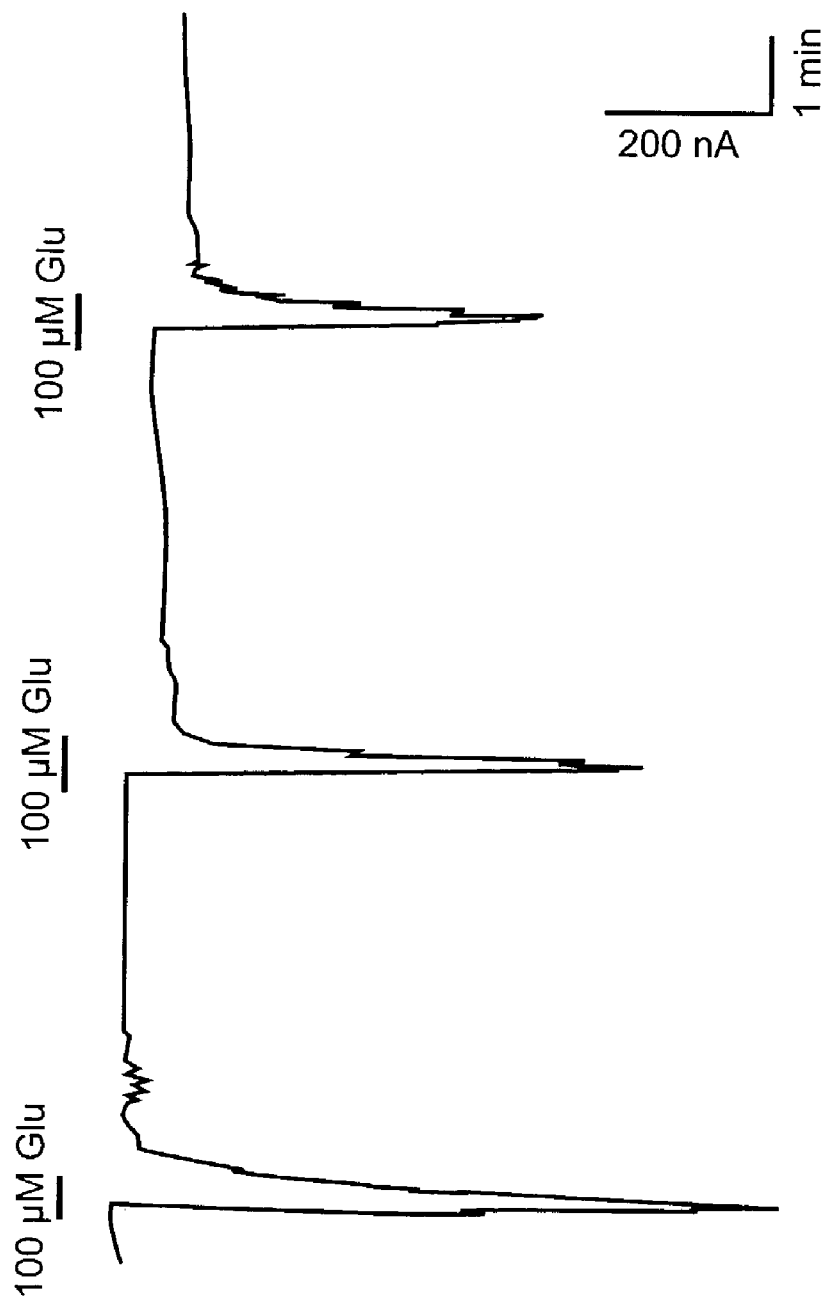
FIG. 3 is a graph depicting the reduced rapid desensitization properties of human mGluR5d expressed in Xenopus oocytes.

Test substances were applied by superfusion at a flow rate of about 5 ml/min. Receptor activation was determined by measuring the increase in calcium-activated chloride current ($I_{Cl}$) Increases in $I_{Cl}$ were quantified by measuring the peak inward current stimulated by activating agent, relative to the holding current at 60 mV. Application of the mGluR activators 100 µM L-glutamate or other agonists, resulted in reversible, oscillatory increases in the calcium-activated chloride current as shown in FIG. 3. These data demonstrate the functional response of the novel human mGluR5d receptor.

Interestingly, in contrast to the other mGluR5 splice variants, mGluR5a and mGluR5b, human mGluR5d displays little desensitization in response to agonists. Gereau & Heineman (1998), *Neuron* 20:143, investigated the molecular mechanisms of rat mGluR5 desensitization and found that both mGluR5a and mGluR5b undergo a relatively rapid PKC-mediated phosphorylation that leads to agonist-induced desensitization of mGluR5-mediated chloride currents in *Xenopus* oocytes. Furthermore, mutations in five PKC consensus sites abolished this desensitization. Two of these sites in the cytoplasmic tail (S881 and S890 in rat mGluR5a, corresponding to S914 and S923 in hmGluR5b, as shown in FIG. 1B) are not present in the novel human mGluR5d splice variant. Repeated application of 10-100 µM L-glutamate or (S)-3,5-dihydroxyphenylglycine (DHPG) to *Xenopus* oocytes expressing hmGluR5d evoked calcium-activated chloride currents, which were only minimally desensitized. The reduced desensitization properties of hmGluR5d splice variant may produce a variety of physiological responses in the CNS during development, normal synaptic function and pathological conditions.

Example 4

Transient and Stable Expression of the Novel Human mGluR5d Splice Variant in Mammalian Cells This example provides a method for the production of stably transfected mammalian cell lines expressing the novel human mGluR, but is not meant to be limiting. Human embryonic kidney cells (293, ATCC, CRL 1573) are grown in a routine manner. Cells are plated in 10 cm cell-culture plates in Dulbecco's modified Eagle's medium (D-MEM) containing 10% fetal bovine serum (FBS) and 1× penicillin-streptomycin (Life Technologies) so that they are approximately 70% confluent after an overnight incubation. To prepare DNA for transfection, the plasmid phmGluR5d (Hyg+) is precipitated with ethanol, rinsed and resuspended in sterile water at a concentration of 1 µg/µl. Ten micrograms of the plasmid DNA is incubated with the liposome formulation LipofectAMINE™ (Life Technologies) for 20 minutes in 1.6 mls of serum-free Opti-MEM (Life Technologies). After the room temperature incubation, 6.4 mls of Opti-MEM is added to the transfection mix. This solution is added to the cells which have been rinsed twice with 8 ml washes of Opti-MEM. The cells and transfection mix are incubated at 37° C. for 5 hours, at which time 8 mls of Opti-MEM/20% FBS is added to bring the FBS concentration to 10%. After an overnight incubation, the medium is changed back to D-MEM with 10% FBS and 2 mM glutamine. These transiently transfected cells can be tested for functional expression of the hmGluR5d receptor. (See Example 6, below.) For stable expression of human mGluR5d, transfections were performed as above, with a few modifications. To prevent tonic activation of hmGluR5d by glutamate that may be released by these cells into the extracellular medium, hmGluR5d was transfected into a clonal HEK293 cell line expressing a glutamate/aspartate transporter (GLAST) from a mammalian expression vector with Zeocin resistance. Desai et al. (1995), *Mol. Pharm.* 48:648. 48 hours post-transfection, these cells are detached with trypsin and replated in medium containing 200 µg/ml hygromycin (Boehringer Mannheim) and 200 µg/ml Zeocin (Invitrogen). Those cells which grow should contain phmGluR5d(Hyg+) which encodes the hygromycin resistance gene. Individual clonal cell lines are recovered and propagated using standard tissue culture techniques. Subcultures of both individual clonal cell lines and pools of many such cell lines can be prepared by dissociation into fresh tissue culture medium, and plating into fresh culture dishes with 1:10 splits of cells. Expression of the novel human mGluR5d splice variant of the present invention in clonal cell lines or pools can be assessed by Northern blot analysis of human mGluR5d mRNA or functionally as in the above experiments by assessing increases in intracellular calcium in response to mGluR5 agonists. Expression can also be assessed by Western blot analysis using the commercially available antibody Anti-Rat MGluR5, polyclonal (Upstate Biotechnology).

Example 5

Transient and Stable Expression of the Chimeric Receptor, hCaR/hmGluR5d in Mammalian Cells This example provides a method for the production of stably transfected mammalian cell lines expressing the chimeric receptor hCaR/hmGluR5d, but is not meant to be limiting. Human embryonic kidney cells (293, ATCC, CRL 1573) are grown in a routine manner. Cells are plated in 10 cm cell-culture plates in Dulbecco's modified Eagle's medium (D-MEM) containing 10% fetal bovine serum (FBS) and 1×penicillin-streptomycin (Life Technologies) so that they are approximately 70% confluent after an overnight incubation. To prepare DNA for transfection, the plasmid phCaR/hmGluR5d(Hyg+) is precipitated with ethanol, rinsed and resuspended in sterile water at a concentration of 1 µg/µl. Ten micrograms of the plasmid DNA is incubated with the liposome formulation LipofectAMINE™ (Life Technologies) for 20 minutes in 1.6 mls of serum-free Opti-MEM (Life Technologies). After the room temperature incubation, 6.4 mls of Opti-MEM is added to the transfection mix. This solution is added to the cells which have been rinsed twice with 5 ml washes of Opti-MEM. The cells and transfection mix are incubated at 37° C. for 5 hours, at which time 6.4 mls of Opti-MEM/20% FBS is added to bring the FBS concentration to 10%. After an overnight incubation, the medium is changed back to D-MEM with 10% FBS and 2 mM glutamine. After an additional 24 hour incubation, cells are detached with trypsin and replated in medium containing 200 µg/ml hygromycin (Boehringer Mannheim). Those cells which grow should contain phCaR/hmGluR5d (Hyg+), which encodes the hygromycin resistance gene. Individual clonal cell lines are recovered and propagated using standard tissue culture techniques. Subcultures of both individual clonal cell lines and pools of many such cell lines can be prepared by dissociation into fresh tissue culture medium, and plating into fresh culture dishes with 1:10 splits of cells. Expression of the novel chimeric receptor hCaR/hmGluR5d mRNA of the present invention in clonal cell lines can be assessed by Northern blot analysis to identify cell lines exhibiting high levels of mRNA expression. Expression can also be assessed by Western blot analysis using the commercially available antibody Anti-Rat mGluR5, polyclonal (Upstate Biotechnology).

Example 6

Figure 4:
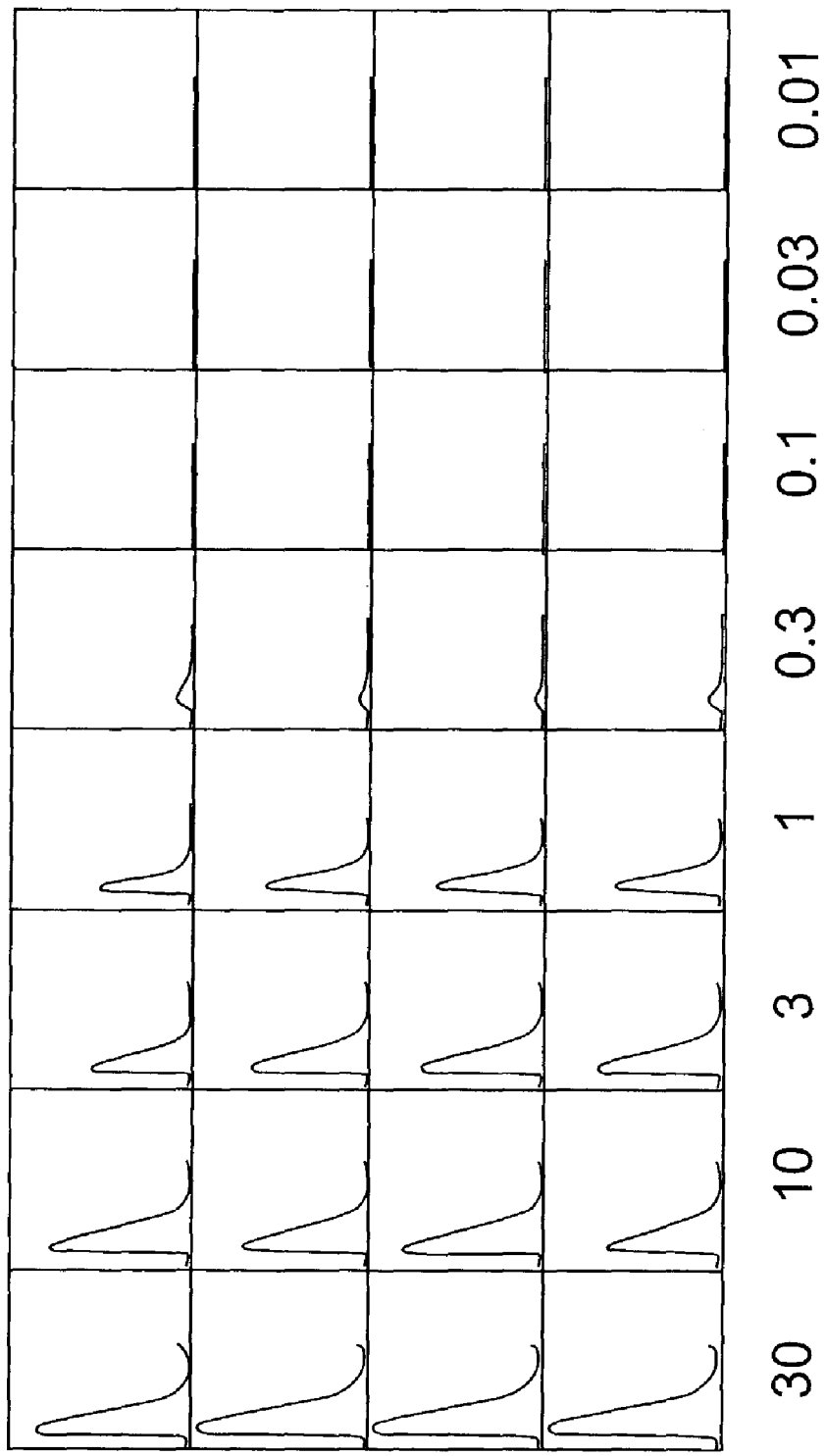
FIG. 4 illustrates functional activation of the hmGluR5d receptor expressed in HEK293 cells with the agonist DHPG.

Functional Activation of the Novel Human mGluR5d Splice Variant Expressed in Mammalian Cells Group I metabotropic glutamate receptors mediate the stimulation of inositol phosphate (IP)/$Ca^{2+}$ signal transduction. Mammalian cell lines stably or transiently transfected with phmGluR5d(Hyg+) can be utilized to examine glutamate- (or other agonist-) induced increases in intracellular calcium. 48 hours post-transfection, cells are detached with trypsin and replated at a density of 4-5×$10^6$ cells/ml in the D-MEM medium in 96 well plates for functional testing. After an additional 24 hour incubation, cells are loaded with the calcium indicator dye Fluo3-AM, and increases in intracellular calcium in response to L-glutamate, (S)-3,5-dihydroxyphenylglycine (DHPG), trans-1-aminocyclopentane-1, 3-dicarboxylic acid (trans-ACPD) and quisqualate are measured using an automated fluorescent imaging plate reader (FLIPR). An example of DHPG activation is shown in FIG. 4.

Example 7

Figure 5:
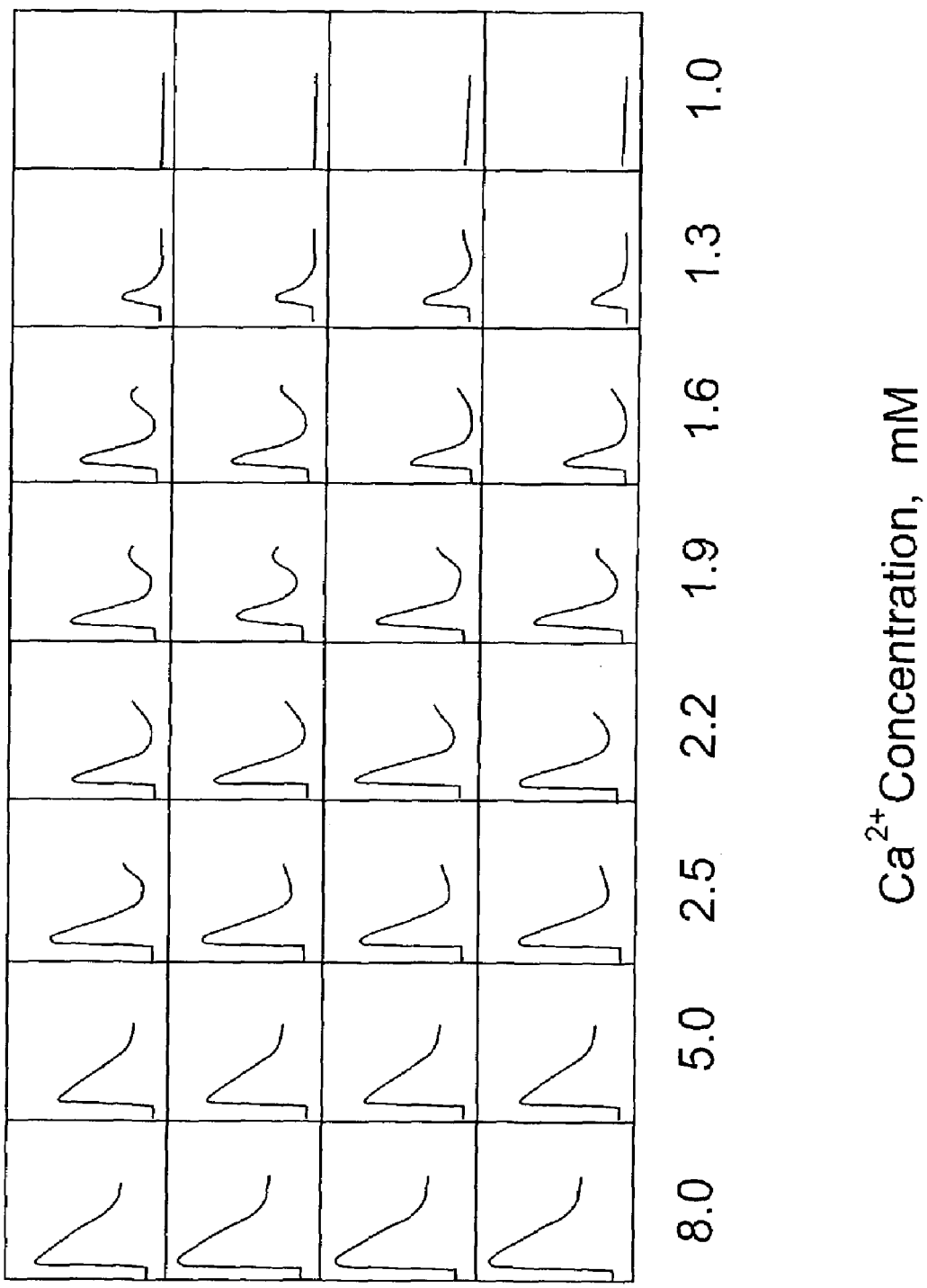
FIG. 5 illustrates functional activation of the hCaR/hmGluR5d chimeric receptor expressed in HEK293 cells by calcium as agonist.

Functional Activation of the Chimeric Receptor, hCaR/hmGluR5d, Expressed in Mammalian Cells The chimeric receptor, hCaR/hmGluR5d, also mediates the stimulation of inositol phosphate (IP)/$Ca^{2+}$ signal transduction. Because this chimera contains the extracellular agonist binding domain of the CaR (Garrett et al. (1995), *J. Biol. Chem*. 270:12919) it is activated by calcium and other agonists of the CaR. Mammalian cell lines stably transfected with phCaR/hmGluR5d(Hyg+) can be utilized to examine calcium- (or other agonist-) induced increases in intracellular calcium. Stably transfected cells are detached with trypsin and replated at a density of 4-5×$10^6$ cells/ml in the D-MEM medium in 96 well plates for functional testing. After an additional 24 hour incubation, cells are loaded with the calcium indicator dye Fluo3-AM and increases in intracellular calcium in response to calcium are measured using an automated fluorescent imaging plate reader (FLIPR). An example of such activation is depicted in FIG. 5.

Example 8

Recombinant Receptor Binding Assays

The following is an example of a rapid screening assay to obtain compounds binding to the glutamate binding site of the novel human mGluR. The screening assay measures the binding of compounds to recombinant mGluRs expressed in stably transfected mammalian cells. O'Hara et al. (1993), *Neuron* 11:41. Cells stably or transiently transfected with the phmGluR5d(Hyg+) expression construct are grown to confluence, rinsed twice with PBS, and harvested by scraping in PBS. The harvested cells are pelleted by centrifugation at 1000 rpm for 5 minutes at 4° C., and frozen at −70° C. Cell membranes are prepared by homogenizing the pellet twice with 50 mM Tris-HCl (pH 7.4), 10 mM EDTA, 0.1 mM phenylmethylsulfonyl fluoride (PMSF), 0.1 mM D,L-benzylsuccinic acid, 10 µg/ml turkey egg white trypsin inhibitor; centrifugation at 30,000×g for 10 minutes at 4° C.; then treatment with DNase and collection by centrifugation. Membrane suspensions are washed twice and resuspended in 50 mM Tris-HCl (pH 7.4), 2.5 mM $CaCl_2$ (Tris/Ca) and the total protein concentration is adjusted to 450-675 µg/ml. For binding assays 25 µls of 200 nM [$^3$H]glutamate (Dupont NEN) or other agonists, such as (S)-3,5-dihydroxyphenylglycine (DHPG), trans-1-aminocyclopentane-1,3-dicarboxylic acid (trans-ACPD) and quisqualate, are added to 225 µls of membrane suspension in the presence or absence of cold competitor (10 mM glutamate) and incubated on ice for 1 hour. Assays are stopped by rapid addition of four mls of ice-cold Tris/Ca buffer and immediate collection of the membranes on Whatman GF/C filters by vacuum filtration. Ten mls of Optiflour (Packard) is added to filters in scintillation vials and the bound radioactivity is quantified by scintillation counting.

The above example is not meant to be limiting. In a broader context, similar binding assays utilizing other radioligands binding to the glutamate binding site or other sites on the human mGluR5d splice variant can be developed by those skilled in the art. Such assays can be utilized to measure the binding of compounds to recombinantly expressed receptors, or receptor fragments. Compounds binding to the novel human mGluRd may then be examined for their ability to modulate one or more functional activities of this human mGluR5d variant.

Example 9

Molecule Screening Using *Xenopus* Oocyte

Oocytes injected with the hmGluR5d cRNA as described in Example 3 provide a system for assessing the actions of novel compounds on the novel human mGluR5d splice variant by measuring increases in the calcium-activated chloride current. Compounds can be assessed for functional activation of human mGluR5d in the absence of glutamate or other known mGluR agonists (agonist activity); accentuation of human mGluR5d activation by glutamate or other known mGluR agonist (positive allosteric modulation); or blockade of human mGluR5d activation by glutamate or other known mGluR5 agonists (antagonist activity).

Example 10

Molecule Screening Using Recombinant Human mGluR5d Splice Variant Expressed in Transfected Cell Lines Cell lines stably or transiently transfected with the novel human mGluR5d expression constructs as described in Example 4 can be utilized to assess the affinity of compounds on the novel human mGluR5d splice variant by utilizing binding assays as described in Example 8. See FIG. 2, in which the reported $EC_{50}$ values for these agonists represent the mean and standard deviation from three independent experiments with multiple (6-18) determinations at each agonist concentration within an experiment. Stably transfected cells expressing hmGluR5d can be assayed in the same manner.

In addition, cell lines transfected with human mGluR5d splice variant expression constructs as described in Example 4 can be utilized to assess the actions of compounds on the novel human mGluR5d splice variant by measuring increases in intracellular calcium in response to the compound.

Compounds can be assessed for functional activation of human mGluR5d splice variant in the absence of glutamate or other known mGluR agonists (agonist activity); accentuation of human mGluR5d splice variant activation by glutamate or other known mGluR agonists (positive allosteric modulation); or blockade of human mGluR5d splice variant activation by glutamate or other known mGluR agonists (antagonist activity).

The invention may be embodied in other specific forms without departing from its essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

We claim:

1. A calcium receptor/metabotropic glutamate receptor chimeric receptor comprising:

an extracellular domain of a G-protein coupled calcium receptor and the seven transmembrane domain and the intracellular cytoplasmic tail domain contained in the amino acid sequence of SEQ ID NO: 2.

2. The chimeric receptor of claim 1, wherein said chimeric receptor comprises the amino acid sequence of SEQ ID NO: 4.

3. An isolated and purified nucleic acid molecule, said nucleic acid molecule comprising a nucleotide sequence that encodes the chimeric receptor of claim 1.

4. The nucleic acid molecule of claim 3, wherein said nucleic acid molecule comprises SEQ ID NO: 3.

* * * * *